US009828438B2

(12) United States Patent
Humphreys et al.

(10) Patent No.: US 9,828,438 B2
(45) Date of Patent: Nov. 28, 2017

(54) DUAL SPECIFICITY ANTIBODY FUSIONS

(71) Applicant: UCB PHARMA S.A., Brussels (BE)

(72) Inventors: David Paul Humphreys, Slough (GB);
Emma Dave, Slough (GB); Laura
Griffin, Slough (GB); Sam Philip
Heywood, Slough (GB)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 15/058,460

(22) Filed: Jul. 6, 2016

(65) Prior Publication Data
US 2016/0311930 A1 Oct. 27, 2016

Related U.S. Application Data

(60) Continuation of application No. 14/101,083, filed on Dec. 9, 2013, now Pat. No. 9,309,327, which is a division of application No. 12/679,873, filed as application No. PCT/GB2008/003331 on Sep. 26, 2008, now Pat. No. 8,629,246.

(30) Foreign Application Priority Data

Sep. 26, 2007 (GB) .................................. 0718832.9
Sep. 26, 2007 (GB) .................................. 0718834.5

(51) Int. Cl.
C07K 16/00 (2006.01)
C07K 16/46 (2006.01)
C07K 16/18 (2006.01)
C07K 16/24 (2006.01)

(52) U.S. Cl.
CPC ............ C07K 16/468 (2013.01); C07K 16/00
(2013.01); C07K 16/18 (2013.01); C07K
16/245 (2013.01); C07K 2317/24 (2013.01);
C07K 2317/31 (2013.01); C07K 2317/522
(2013.01); C07K 2317/54 (2013.01); C07K
2317/55 (2013.01); C07K 2317/569 (2013.01);
C07K 2317/64 (2013.01); C07K 2317/92
(2013.01)

(58) Field of Classification Search
None
See application file for complete search history.

(56) References Cited

U.S. PATENT DOCUMENTS

| 5,959,083 | A | 9/1999 | Bosslet et al. |
| 5,972,901 | A | 10/1999 | Ferkol |
| 6,066,719 | A | 5/2000 | Zapata |
| 6,239,259 | B1 | 5/2001 | Davis et al. |
| 6,267,964 | B1 | 7/2001 | Nygren et al. |
| 6,670,453 | B2 | 12/2003 | Frenken et al. |
| 6,809,185 | B1 | 10/2004 | Schoonjans et al. |
| 7,074,405 | B1 | 7/2006 | Hansen et al. |
| 7,129,330 | B1 | 10/2006 | Little et al. |
| 7,612,181 | B2 | 11/2009 | Wu et al. |
| 2002/0004587 | A1 | 1/2002 | Miller et al. |
| 2002/0010334 | A1 | 1/2002 | Li |
| 2002/0150559 | A1 | 10/2002 | DeBoer et al. |
| 2004/0219643 | A1 | 11/2004 | Winter et al. |
| 2004/0259156 | A1 | 12/2004 | Zhu |
| 2005/0079170 | A1 | 4/2005 | Le Gall et al. |
| 2006/0025576 | A1 | 2/2006 | Miller et al. |
| 2006/0083747 | A1 | 4/2006 | Winter et al. |
| 2006/0106203 | A1 | 5/2006 | Winter et al. |
| 2006/0257406 | A1 | 11/2006 | Winter et al. |
| 2006/0280734 | A1 | 12/2006 | Winter et al. |
| 2007/0004909 | A1 | 1/2007 | Johnson et al. |
| 2007/0065440 | A1 | 3/2007 | Tomlinson et al. |
| 2007/0071675 | A1 | 3/2007 | Wu et al. |
| 2009/0148447 | A1 | 6/2009 | Ledbetter et al. |

FOREIGN PATENT DOCUMENTS

| EP | 0368684 | 5/1990 |
| EP | 1136556 | 9/2001 |
| EP | 2014680 | 1/2009 |
| EP | 2050764 | 4/2009 |
| NO | WO 2005118642 | 12/2005 |
| WO | 88/01649 | 4/1988 |
| WO | 91/01743 | 2/1991 |
| WO | 93/11161 | 6/1993 |
| WO | 94/04690 | 3/1994 |
| WO | 94/09131 | 4/1994 |
| WO | WO 9409131 | 4/1994 |
| WO | 94/13804 | 6/1994 |
| WO | 95/09917 | 4/1995 |
| WO | 97/38102 | 10/1997 |
| WO | 01/45746 | 6/2001 |
| WO | 01/77342 | 10/2001 |
| WO | 01/85795 | 11/2001 |
| WO | 02/02773 | 1/2002 |
| WO | 02/02781 | 1/2002 |

(Continued)

OTHER PUBLICATIONS

Wunder, et al., "Albumin-Base drug delivery as a Novel Therapeutic Approach for Rheumatoid Arthritis", The Journal of Immunology, 170:4793-4801 (2003).
Xie, et al., "A trivalent anti-erbB2/anti-CD16 bispecific antibody retargeting NK cells against human breast cancer cells", Biochemical and Biophysical Research Communication, 311:307-312 (2003).
Xie, et al., "A new format of Bispecific antibody: highly efficient heterodimerization, expression and tumor cell lysis", Journal of Immunol., Methods 296:95-101 (2005).

(Continued)

Primary Examiner — Brad Duffy
(74) Attorney, Agent, or Firm — McDonnell Boehnen Hulbert & Berghoff LLP

(57) ABSTRACT

The present invention provides dual specificity antibody fusion proteins comprising an antibody Fab or Fab' fragment with specificity for an antigen of interest, said fragment being fused to at least one single domain antibody which has specificity for a second antigen of interest.

8 Claims, 9 Drawing Sheets

(56) References Cited

FOREIGN PATENT DOCUMENTS

Figure 1:
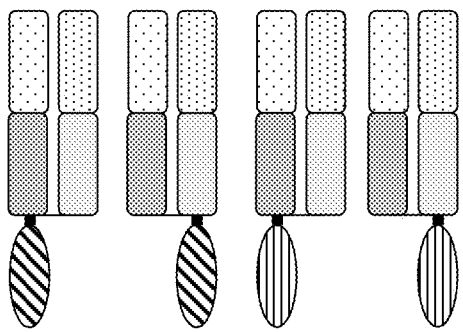

| | | |
|---|---|---|
| WO | 02/08293 | 1/2002 |
| WO | 02/076489 | 10/2002 |
| WO | 2004/001064 | 12/2003 |
| WO | 2004/003019 | 1/2004 |
| WO | 2004/032832 | 4/2004 |
| WO | 2004/041863 | 5/2004 |
| WO | 2004/058820 | 7/2004 |
| WO | 2005/000899 A2 | 1/2005 |
| WO | 2006/122787 | 11/2006 |
| WO | 2007/024715 | 3/2007 |
| WO | 2007/085837 | 8/2007 |
| WO | 2007/095338 | 8/2007 |
| WO | 2007/106120 | 9/2007 |
| WO | 2007/109254 | 9/2007 |
| WO | 2007/146968 | 12/2007 |
| WO | 2008/003103 | 1/2008 |
| WO | 2009/018386 | 2/2009 |
| WO | 2009/021754 | 2/2009 |
| WO | 2009/040562 | 4/2009 |
| WO | 2009/052081 | 4/2009 |
| WO | 2009/068628 | 6/2009 |
| WO | 2009/068630 | 6/2009 |
| WO | 2009/068649 | 6/2009 |
| WO | 2009/080254 | 7/2009 |
| WO | 2010/065882 | 6/2010 |
| WO | 2010/136172 | 12/2010 |
| WO | 2011/030107 | 3/2011 |
| WO | 2011/036460 A1 | 3/2011 |

OTHER PUBLICATIONS

Young, et al., "Thermal stabilization of a single-chain Fv antibody fragment by introduction of a disulfide bond", FEBS Leters, 377:135-139 (1995).

Zalipsky, "Chemistry of polyethylene glycol conjugates with biologically active molecules", Advanced Drug Delivery Reviews, 16"157-182 (1995).

Zhu, et al., "Remodelling domain interfaces to enhance heterodimer formation", Protein Science, 6:781-788 (1997).

Demarst, et al., "Antibody therapeutics, antibody engineering, and the merits of protein stability", Current Opinion in drug Discovery & Development, 11:675-687 (2008).

Desplancq, et al., "Multimerization behaviour of single chain Fv variants for the tumour-binding antibody B72.3", Protein Engineering, 7:1027-1033 (1994).

Fischer, et al., "Bispecific Antibodies: Molecules That Enable Novel Therapeutic Strategies", pathobiology 74:3-14 (2007).

Glockshuber, et al., "A comparison of stratagies to stabilize immunoglobulin Fv-fragments", biochemistry 29:1362-1367 (1990).

Hao, et al., "Improved stability and yield of Fv targeted superantigen by introducing both linker and disulfide bond into the targeting moiety", Biochemie, 87:661-667 (2005) Abstract Only.

Holt, et al., "Anti-serum albumin domain antibodies for extending the half-lives of short lived drugs", Protein Engineering, Design and Selection, 21:283-288 (2008).

Huston, et al., "Protein engineering of antibody binding sites: Recovery of specific activity and an anti-digoxin single-chain Fv analogue produced in E coli", Proc. Natl. Acad. Sci., 85:5879-5883 (1988).

Adams, et al., "Avidity-mediated enhancement of in vivo tumor targeting by single-chain Fv dimmers", Clinical Cancer Research 12:1599-1605 (2006).

Albrecht, et al., "Monospecific bivalent scFv-SH Effect on linker length and location of an engineered cysteine on production, antigen binding and free SH accessibility", J. Immunol. Methods, 320:100-116 (2006).

Anderson, et al., "The conserved histadine 166 residue of the human neonatal Fc receptor heavy chain is critical or the pH-dependent binding to albumin", Eru. J. Immunol., 26:3044-3051 (2006).

Brinkman, "A recombinant immunotoxin containing a disulfide-stabilised Fv fragment", Proc. Natl Acad Sci,90:7538-7542 (1993).

Butler, et al., "Effect of Sheep Digoxin-Specific Antibodies and their Fab fragments on Digoxin Pharmacokinetics in Dogs", JCI., 59:345-359 (1977).

Chapman, et al., "Therapeutic antibody fragments with prolonged in vivo half-life", Nature Biotech, 17:780-783 (1999).

Coppieters, et al., "Formatted anti-tumor necrosis factor alpha VHH proteins derived from camelids show superior potency and targeting to inflamed joints in a murine model of collagen-induced arthritis", Arthritis and Rheumatism, 54:1856-1866 (2006).

Dennis, et al., "Albumin binding as a general strategy for improving the pharmacokinetics of proteins", Journal of Biological Chemistry, 277:35035-35043 (2002).

Dennis, et al., "Imaging Tumors with an Albumin-Binding Fab, a Novel Tumor-Targeting Agent", Cancer Res, 67:254-261 (2007).

Shen, et al., "Single variable domain antibody as a versatile building block for the construction of IgG-like bispecific antibodies", Journal of Immunologcal Methods, 318:65-74 (2007).

Harmsen, et al., "Prolonged in vivo residence times of llama single0domain antibody fragments in pigs bybinding to procine immunoglobulins", Vaccine Buttersowrth Scientific, 23:4926-4934 (2005).

Wu, et al., "Simultaneous targeting of multiple disease mediators by a dual-variable-domain immunoglobulin", nature Biotech, 25:1290-1297 (2007).

Buchner et al., "Renaturation, purification and characterization of recombinant Fab-fragments produced in *Escherichia coli*," Biotechnology (NY) 9(2): 157-62 (1991).

Honegger, "Engineering antibodies for stability and efficient folding," Handb Exp Pharmacol. (181): 47-68 (2008).

Huang et al., "Mono and bivalent binding of a scFv and covalent diabody to murine laminin-1 using radioiodinated proteins and SPR measurements: effects on tissue retention in vivo," J Immunol Methods 313(1-2): 149-60 (2006).

Hust et al., "Single chain Fab (scFab) fragment," BMC Biotechnol. 8;7: 14 (2007).

Kufer et al., "A revival of bispecific antibodies," Trends Biotechnol. 22(5): 238-44 (2004).

Reiter et al., "Engineering interchain disulfide bonds into conserved framework regions of Fv fragments: improved biochemical characteristics of recombinant immunotoxins containing disulfide-stabilized Fv," Protein Eng. 7(5): 697-704 (1994).

Rothlisberger et al., "Domain interactions in the Fab fragment: a comparative evaluation of the single-chain Fv and Fab format engineered with variable domains of different stability," J Mol Biol. 347(4): 773-89 (2005).

Skerra, "A general vector, pASK84, for cloning, bacterial production, and single-step purification of antibody Fab fragments," Gene 141(1): 79-84 (1994).

Worn & Pluckthun, "Stability engineering of antibody single-chain Fv fragments," J Mol Biol. 305(5): 989-1010 (2001).

Wu et al., "Molecular construction and optimization of anti-human IL-1alpha/beta dual variable domain immunoglobulin (DVD-Ig) molecules," MAbs 1(4): 339-47 (2009).

Coleman, et al. pro. Exp & Purr., 32:246-251(2003).

Ocructt, et al., "A Modular IgG-scFv bispecific antibody topology", Protein Eng. , Des., & Sel., 23:221-228 (2010).

Ionescu, et al., "Contribut8on of variable domains of the stability of humanzied IgG1 antibodies", Journal of Pharmaceutical Science, 97:1414-1426 (2007).

Jung, et al., Design of Interchain Disulfide Bonds in the Framework Region of the Fv Fragment of the monoclonal antibody b3, 1994, Proteins, 19:35-47 (1994).

Keystone, et al., Certolizumab Pegol Plus Methotrexate Is Significantly More Effective than Placebo Plus Methotrexate in Active Rhuematoid Arthritis:, Arthritis and Rheumatism 58:3319-3329 (2008).

Kitamura, et al., "Chemical Engineering of the Monoclonal antibody A7 by Polyethylene Glycol for targeting Cancer Chemotherapy", cancer research 51:4310-4315 (1991).

Kortt, et al., "Dimeric and trimeric antibodies: high avidity scFvs for cancer targetting", Biol. Eng.,18:95-108 (2001).

(56) References Cited

OTHER PUBLICATIONS

Kuan, et al., "Pseudomonas Exotoxin A mutants", J. Biol. Chem, 269:7610-7616.

Le Gall, et al., "Effect of linker sequences between the antibody variable domains on the formation, stability and biological activity of bispecific tandem diabody", Protein Engineering Design and selection 17:357-366 (2004).

Luo et al, "VI-Linker-Vh Orientation-Dependent Expression of Single Chain Fv Containing an Engineered Disulfide-Stabilized Bond in the Framework Regions", Journal of Biochemistry, 118:825-831 (1995).

Mabry, et al, "Engineering of stable bispecific antibodies targeting IL-17A and IL-23", Protein Engineering Design and Selection, 23:115-127 (2009).

Marvin, et al, "Recombinant approaches to IgG-like specific antibodies", Acta Pharma Sinica, 26:649-658 (2005).

Mimura, et al, "The influence of glycosylation on the thermal stability of effector function expression of human IgG1-Fc properties of a series of truncated glycoforms", Molecular Immunology, 37:697-706 (2000).

Nieba, et al., "Disrupting the hydrophobic patches at the antibody/variable constant domain interface: improved in vivo folding and physical characterization of an engineered scFv fragment", Protein Eingineering 10:435-444 (1997).

Nguyen, et al., "The pharmacokinetics of an albumin-binding Fab (AB.Fab) can be modulated as a function of affinity for albumin", Protein Engineering, Design and Selection, 19:291-297 (2006).

Peters, "Serum Albumin", Advances in Protein Chemistry, 37:161-245 (1985).

Pluckthun, et al., "New protein engineering approaches to multivalent and bispecific antibody fragments", Immunotechnology, 3:83-105 (1997).

Rajagopal, et al., "A form of anti-Tac (Fv) which is both single chain and disulphide stabilized: a comparison with its single-chain and disulphide-stabilised homologs", Protein Engineering, 10:1453-1459 (1997).

Reff, et al., "Future of Monoclonal antibodies in the treatment of hematologic malignancies", Cancer Control, 9:152-166 (2002).

Reiter, et al.,. "Stabilization of the Fv Fragment in Recombinant Immunotoxins by Disulfide Bonds Engineered into Conserved Framework Regions", biochemistry American chemical Society, 33:5451-5459 (1994).

Reiter, et al., "Improved binding and antitumor activity of a recombinant anti-erbB2 immunotoxin by disulfide stabilization of the Fv fragment", The journal of Biological Chemistry, 269:18327-18331 (1994).

Reiter, et al., "Engineering Antibody Fv fragments for cancer detection and therapy: Disulfide-stabilised Fv fragments", Nature Biotechnology, 14:1239-1245 (1996).

Roovers, et al., "Efficient inhibition of EGFR signaling and of tumor growth by antagonistic and anti-EGFR antibodies", Cancer Immunol. Immunther. 56:303-317 (2007).

Schmidt, et al., "Suppression of metastasis formation by a recombinant single chain antibody-toxin targeted to full-length and oncogenic variant EGF receptors", Oncogene 18:1711-1721 (1999).

Schmiedl, et al., "Recombinant variants of antibody 138H11 against human gamma-glutamyltransferase for targeting renal cell carcinoma", Human Antibodies, 15:15:81-94 (2004).

Schoonjans, et al., "Fab chains as an efficient heterodimerization scaffold for the production of recombinant bispecific and trispecific antibody derivatives", J. Immunol, 165:7050-7057 (2000).

Schoonjans, et al., "A new model for intermediate molecular weight bispecific and trispecific antibodies by efficient heterodimerization of single chain variable domains through fusion to Fab-chain", Biomolecular Engineering, 17:193-202.

Schoonoghe, et al., "Efficient production of human bivalent and trivalent anti-MUC1 Fab-scFV antibodies in Pichia pastoris", BMC Biotechnology, 9:70 (2009).

Segal, et al., "Bispecific antibodies in cancer therapy", Current Opinion in Immunology, 11:558-562 (1999).

Shen, et al., "Single variable domain antibody as a versatile building block for the construction of IgG-like bispecific antibodies", Journal of Immunological Methods, 318:65-74 (2007).

Smith, et al., "Prolonged in vivo residence times of antibody fragments associated with albumin", Bioconjugate Chemistry, 12:750-756 (2001).

Staerz, et al., "Hybrid antibodies can target sites for attack by T cells", Nature 18:628-630 (1985).

Tijink, et al, "Improved tumor targeting of anti-epidermal growth factor receptor nanobodies through albumin binding: taking advantage of modular nanobody technology" Molecular Cancer Therapeutics, 7:2288-2297 (2008).

Tolmachev, et al., "Radionuclide Therapy of HER2-Positive Microxenografts using a 177Lu-labeled HER2-specific Antibody Molecule", Cancer Res, 67:2773-2785 (2007).

Uno, et al, "Eradiction of established tumors in mice by a combination antibody-based therapy", Nature medicine 12:693-698 (2006).

Vaezin, et al., "Optimizing the Generation of Recombinant Single-Chain Antibodies Against Placental Alkaline Phosphatase", hybridoma 4:181-192 (2006).

Waldman, et al., "Metabolism of Immunoglobulins", Progr. Allergy, 13:1-110 (1969).

Wang, et al., "Polyethylene Glycol-modified Chimeric Toxin Composed of Transforming Growth Factor alpha and Psuedomonas Exotoxin", Cancer Research, 53:4588-4594 (1993).

Willems, et al., "Optimizing expression and purification from cell culture medium of trispecific recombinant antibody derivatives", J. Chromatography B, 786:161-176 (2003).

Whitlow, et al., "Multivalent Fvs: characterization of single-chain Fv oligomers and preparation of a bispecfic FV", Protein Engineering, 7:1017-1026 (1994).

dAbL or dAbH are linked to the C-terminus of the constant region of either the light or heavy chain via a linker (—).

Variable region of light chain ▭ or heavy chain ▭ . Constant regions cKappa ▭ and CH1 ▭ . Domain antibody fragments dAbL ⬯ and dAbH ⬯ dAbL and dAbH are linked to the C-terminus of the constant region of each chain so that a LC-dAbL or LC-dAbH fusion is paired with either the HC-dAbL or HC-dAbH.

Variable region of light chain [ ] or heavy chain [ ]. Constant regions cKappa [ ] and CH1 [ ]. Domain antibody fragments, dAbL and dAbH.

Figure 5 a) dAbH1
EVQLLESGGGLVQPGGSLRLSCAVSGIDLSNYAINWVRQAPGKGLEWIGIIWA
SGTTFYATWAKGRFTISRDSTTVYLQMNSLRAEDTAVYYCARTVPGYSTAPY
FDLWGQGTLVTVSS (SEQ ID NO:52)

b) dAbL1
DIVMTQSPSSVSASVGDRVTITCQSSPSVWSNFLSWYQQKPGKAPKLLIYEAS
KLTSGVPSRFKGSGSGTDFTLTISSLQPEDFATYYCGGGYSSISDTTFGGGTKV
EIK (SEQ ID NO:53)

c) dAbH2
EVQLVESGGGLVQPGGSLRLSCAVSGFSLSRYAMTWVRQAPGKGLEWIGTIT
TGGNTNYANWAKGRFTISKDSTTVYLQMNSLRAEDTAVYYCARGGYVSYA
DATELSLWGQGTLVTVSS (SEQ ID NO:54)

d) dAbL2
DIVMTQSPSTLSASVGDRVTITCQASQSIGSRLAWYQQKPGKAPKLLIYYAST
VASGVPSRFKGSGSGTEFTLTISSLQPDDFATYYCQSYDYSSSSSYAFGGGTKV
EIK (SEQ ID NO:55)

dAbH1
e)  CDRH1:    GIDLSNYAIN (SEQ ID NO:56)
f)  CDRH2:    IIWASGTTFYATWAKG (SEQ ID NO:57)
g)  CDRH3:    TVPGYSTAPYFDL (SEQ ID NO:58)

dAbL1
h)  CDRL1:    QSSPSVWSNFLS (SEQ ID NO:59)
i)  CDRL2:    EASKLTS (SEQ ID NO:60)
j)  CDRL3:    GGGYSSISDTT (SEQ ID NO:61)

dAbH2
k)  CDRH1:    GFSLSRYAMT (SEQ ID NO:62)
l)  CDRH2:    TITTGGNTNYANWAKG (SEQ ID NO:63)
m)  CDRH3:    GGYVSYADATELSL (SEQ ID NO:64)

dAbL2
n)  CDRL1:    QASQSIGSRLA (SEQ ID NO:65)
o)  CDRL2:    YASTVAS (SEQ ID NO:66)
p)  CDRL3:    QSYDYSSSSSYA (SEQ ID NO:67)

FIGURE 6

A. FabB-dAbH1 (CH1-G₄Sx2)

FAB-B HEAVY CHAIN VARIABLE DOMAIN +

ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC<u>GGG
GSGGGGS</u>EVQLLESGGGLVQPGGSLRLSCAVSGIDLSNYAINWVRQAPGKGL
EWIGIIWASGTTFYATWAKGRFTISRDSTTVYLQMNSLRAEDTAVYYCARTV
PGYSTAPYFDLWGQGTLVTVSS (SEQ ID NO:68)

B. FabB-dAbH2 (CH1-G₄Sx2)

FAB-B HEAVY CHAIN VARIABLE DOMAIN +

ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC<u>GGG
GSGGGGS</u>EVQLVESGGGLVQPGGSLRLSCAVSGFSLSRYAMTWVRQAPGKG
LEWIGTITTGGNTNYANWAKGRFTISKDSTTVYLQMNSLRAEDTAVYYCAR
GGYVSYADATELSLWGQGTLVTVSS (SEQ ID NO:69)

C. FabB-dAbL1 (CH1-G₄Sx2)

FAB-B HEAVY CHAIN VARIABLE DOMAIN +

ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC<u>GGG
GSGGGGS</u>DIVMTQSPSSVSASVGDRVTITCQSSPSVWSNFLSWYQQKPGKAP
KLLIYEASKLTSGVPSRFKGSGSGTDFTLTISSLQPEDFATYYCGGGYSSISDTT
FGGGTKVEIK (SEQ ID NO:70)

D. FabB-dAbL2 (CH1-G₄Sx2)

FAB-B HEAVY CHAIN VARIABLE DOMAIN +

ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC<u>GGG
GSGGGGS</u>DIVMTQSPSTLSASVGDRVTITCQASQSIGSRLAWYQQKPGKAPKL
LIYYASTVASGVPSRFKGSGSGTEFTLTISSLQPDDFATYYCQSYDYSSSSSYA
FGGGTKVEIK (SEQ ID NO:71)

E. FabB-dAbL1 (CK-G₄Sx2)

FABB- LIGHT CHAIN VARIABLE DOMAIN +

RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRG
ECGGGGSGGGGSDIVMTQSPSSVSASVGDRVTITCQSSPSVWSNFLSWYQQK

FIGURE 6, CONTINUATION

PGKAPKLLIYBASKLTSGVPSRFKGSGSGTDFTLTISSLQPEDFATYYCGGGYS
SISDTTFGGGTKVEIK (SEQ ID NO:72)

F. FabB-dAbL2 (CK-G₄Sx2)

FABB- LIGHT CHAIN VARIABLE DOMAIN +

RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRG
EC*GGGGSGGGGS*DIVMTQSPSTLSASVGDRVTITCQASQSIGSRLAWYQQKP
GKAPKLLIYYASTVASGVPSRFKGSGSGTEFTLTISSLQPDDFATYYCQSYDYS
SSSSYAFGGGTKVEIK (SEQ ID NO:73)

Figure 7:

Fab'A heavy chain
MKKTAIAIAVALAGFATVAQAEVQLVESGGGLVQPGGSLRLSCAFSGFSLSTS
GVGVGWVRQAPGKGLEWVAHIWWDGDESYNPSLKTQFTISKDTSKNTVYL
QMNSLRAEDTAVYYCARNRYDPPWFVDWGQGTLVTVSSASTKGPSVFPLAP
SSKSTSGGTAALGCLVKDYFPEPVTVSWNSGALTSGVHTFPAVLQSSGLYSLS
SVVTVPSSSLGTQTYICNVNHKPSNTKVDKKVEPKTCDKTHTCPPCPA (SEQ
ID NO:74)

FabA light chain
MKKTAIAIAVALAGFATVAQADIQMTQSPSSLSASVGDRVTITCRASQDISNY
LSWYQQKPGKAPKLLIYYTSKLHSGVPSRFSGSGSGTDYTLTISSLQPEDFATY
YCQQGKMLPWTFGQGTKVEIKRTVAAPSVFIFPPSDEQLKSGTASVVCLLNNF
YPREAKVQWKVDNAVQSGNSQESVTEQDSKDSTYSLSSTLTLSKADYEKHK
VYACEVTHQGLSSPVTKSFNRGEC (SEQ ID NO:75)

Fab'A heavy chain (modified hinge linker)
MKKTAIAIAVALAGFATVAQAEVQLVESGGGLVQPGGSLRLSCAFSGFSLSTS
GVGVGWVRQAPGKGLEWVAHIWWDGDESYNPSLKTQFTISKDTSKNTVYL
QMNSLRAEDTAVYYCARNRYDPPWFVDWGQGTLVTVSSASTKGPSVFPLAP
SSKSTSGGTAALGCLVKDYFPEPVTVSWNSGALTSGVHTFPAVLQSSGLYSLS
SVVTVPSSSLGTQTYICNVNHKPSNTKVDKKVEPKTCDKTHTS (SEQ ID
NO:76)

FabA heavy chain
MKKTAIAIAVALAGFATVAQAEVQLVESGGGLVQPGGSLRLSCAFSGFSLSTS
GVGVGWVRQAPGKGLEWVAHIWWDGDESYNPSLKTQFTISKDTSKNTVYL
QMNSLRAEDTAVYYCARNRYDPPWFVDWGQGTLVTVSSASTKGPSVFPLAP
SSKSTSGGTAALGCLVKDYFPEPVTVSWNSGALTSGVHTFPAVLQSSGLYSLS
SVVTVPSSSLGTQTYICNVNHKPSNTKVDKKVEPKTC (SEQ ID NO:77)

SEQUENCE LISTING

```
<160> NUMBER OF SEQ ID NOS: 77

<210> SEQ ID NO 1
<211> LENGTH: 7
<212> TYPE: PRT
<213> ORGANISM: Artificial
<220> FEATURE:
<223> OTHER INFORMATION: linker

<400> SEQUENCE: 1

Ser Gly Gly Gly Gly Ser Glu
1               5

<210> SEQ ID NO 2
<211> LENGTH: 6
<212> TYPE: PRT
<213> ORGANISM: Artificial
<220> FEATURE:
<223> OTHER INFORMATION: linker

<400> SEQUENCE: 2

Asp Lys Thr His Thr Ser
1               5

<210> SEQ ID NO 3
<211> LENGTH: 5
<212> TYPE: PRT
<213> ORGANISM: Artificial
<220> FEATURE:
<223> OTHER INFORMATION: linker

<400> SEQUENCE: 3

Gly Gly Gly Gly Ser
1               5

<210> SEQ ID NO 4
<211> LENGTH: 11
<212> TYPE: PRT
<213> ORGANISM: Artificial
<220> FEATURE:
<223> OTHER INFORMATION: linker

<400> SEQUENCE: 4

Ala Ala Ala Gly Ser Gly Gly Ala Ser Ala Ser
1               5                   10

<210> SEQ ID NO 5
```

```
<211> LENGTH: 16
<212> TYPE: PRT
<213> ORGANISM: Artificial
<220> FEATURE:
<223> OTHER INFORMATION: linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 5

Ala Ala Ala Gly Ser Gly Xaa Gly Gly Gly Ser Gly Ala Ser Ala Ser
1               5                   10                  15

<210> SEQ ID NO 6
<211> LENGTH: 13
<212> TYPE: PRT
<213> ORGANISM: Artificial
<220> FEATURE:
<223> OTHER INFORMATION: linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 6

Ala Ala Ala Gly Ser Gly Xaa Ser Gly Ala Ser Ala Ser
1               5                   10

<210> SEQ ID NO 7
<211> LENGTH: 28
<212> TYPE: PRT
<213> ORGANISM: Artificial
<220> FEATURE:
<223> OTHER INFORMATION: linker

<400> SEQUENCE: 7

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 8
<211> LENGTH: 11
<212> TYPE: PRT
<213> ORGANISM: Artificial
<220> FEATURE:
<223> OTHER INFORMATION: linker

<400> SEQUENCE: 8

Ala Thr Thr Thr Gly Ser Ser Pro Gly Pro Thr
1               5                   10

<210> SEQ ID NO 9
<211> LENGTH: 6
<212> TYPE: PRT
<213> ORGANISM: Artificial
<220> FEATURE:
<223> OTHER INFORMATION: linker

<400> SEQUENCE: 9

Ala Thr Thr Thr Gly Ser
1               5

<210> SEQ ID NO 10
<211> LENGTH: 21
<212> TYPE: PRT
<213> ORGANISM: Artificial
```

```
<220> FEATURE:
<223> OTHER INFORMATION: linker

<400> SEQUENCE: 10

Glu Pro Ser Gly Pro Ile Ser Thr Ile Asn Ser Pro Ser Lys Glu
1               5                   10                  15

Ser His Lys Ser Pro
            20

<210> SEQ ID NO 11
<211> LENGTH: 15
<212> TYPE: PRT
<213> ORGANISM: Artificial
<220> FEATURE:
<223> OTHER INFORMATION: linker

<400> SEQUENCE: 11

Gly Thr Val Ala Ala Pro Ser Val Phe Ile Phe Pro Pro Ser Asp
1               5                   10                  15

<210> SEQ ID NO 12
<211> LENGTH: 15
<212> TYPE: PRT
<213> ORGANISM: Artificial
<220> FEATURE:
<223> OTHER INFORMATION: linker

<400> SEQUENCE: 12

Gly Gly Gly Gly Ile Ala Pro Ser Met Val Gly Gly Gly Gly Ser
1               5                   10                  15

<210> SEQ ID NO 13
<211> LENGTH: 15
<212> TYPE: PRT
<213> ORGANISM: Artificial
<220> FEATURE:
<223> OTHER INFORMATION: linker

<400> SEQUENCE: 13

Gly Gly Gly Gly Lys Val Glu Gly Ala Gly Gly Gly Gly Gly Ser
1               5                   10                  15

<210> SEQ ID NO 14
<211> LENGTH: 15
<212> TYPE: PRT
<213> ORGANISM: Artificial
<220> FEATURE:
<223> OTHER INFORMATION: linker

<400> SEQUENCE: 14

Gly Gly Gly Gly Ser Met Lys Ser His Asp Gly Gly Gly Gly Ser
1               5                   10                  15

<210> SEQ ID NO 15
<211> LENGTH: 15
<212> TYPE: PRT
<213> ORGANISM: Artificial
<220> FEATURE:
<223> OTHER INFORMATION: linker

<400> SEQUENCE: 15

Gly Gly Gly Gly Asn Leu Ile Thr Ile Val Gly Gly Gly Gly Ser
1               5                   10                  15

<210> SEQ ID NO 16
<211> LENGTH: 15
```

-continued

```
<212> TYPE: PRT
<213> ORGANISM: Artificial
<220> FEATURE:
<223> OTHER INFORMATION: linker

<400> SEQUENCE: 16

Gly Gly Gly Gly Val Val Pro Ser Leu Pro Gly Gly Gly Gly Ser
1               5                   10                  15

<210> SEQ ID NO 17
<211> LENGTH: 12
<212> TYPE: PRT
<213> ORGANISM: Artificial
<220> FEATURE:
<223> OTHER INFORMATION: linker

<400> SEQUENCE: 17

Gly Gly Glu Lys Ser Ile Pro Gly Gly Gly Ser
1               5                   10

<210> SEQ ID NO 18
<211> LENGTH: 18
<212> TYPE: PRT
<213> ORGANISM: Artificial
<220> FEATURE:
<223> OTHER INFORMATION: linker

<400> SEQUENCE: 18

Arg Pro Leu Ser Tyr Arg Pro Pro Phe Pro Phe Gly Phe Pro Ser Val
1               5                   10                  15

Arg Pro

<210> SEQ ID NO 19
<211> LENGTH: 18
<212> TYPE: PRT
<213> ORGANISM: Artificial
<220> FEATURE:
<223> OTHER INFORMATION: linker

<400> SEQUENCE: 19

Tyr Pro Arg Ser Ile Tyr Ile Arg Arg Arg His Pro Ser Pro Ser Leu
1               5                   10                  15

Thr Thr

<210> SEQ ID NO 20
<211> LENGTH: 18
<212> TYPE: PRT
<213> ORGANISM: Artificial
<220> FEATURE:
<223> OTHER INFORMATION: linker

<400> SEQUENCE: 20

Thr Pro Ser His Leu Ser His Ile Leu Pro Ser Phe Gly Leu Pro Thr
1               5                   10                  15

Phe Asn

<210> SEQ ID NO 21
<211> LENGTH: 18
<212> TYPE: PRT
<213> ORGANISM: Artificial
<220> FEATURE:
<223> OTHER INFORMATION: linker

<400> SEQUENCE: 21

Arg Pro Val Ser Pro Phe Thr Phe Pro Arg Leu Ser Asn Ser Trp Leu
```

Pro Ala

<210> SEQ ID NO 22
<211> LENGTH: 18
<212> TYPE: PRT
<213> ORGANISM: Artificial
<220> FEATURE:
<223> OTHER INFORMATION: linker

<400> SEQUENCE: 22

Ser Pro Ala Ala His Phe Pro Arg Ser Ile Pro Arg Pro Gly Pro Ile
1               5                   10                  15

Arg Thr

<210> SEQ ID NO 23
<211> LENGTH: 18
<212> TYPE: PRT
<213> ORGANISM: Artificial
<220> FEATURE:
<223> OTHER INFORMATION: linker

<400> SEQUENCE: 23

Ala Pro Gly Pro Ser Ala Pro Ser His Arg Ser Leu Pro Ser Arg Ala
1               5                   10                  15

Phe Gly

<210> SEQ ID NO 24
<211> LENGTH: 18
<212> TYPE: PRT
<213> ORGANISM: Artificial
<220> FEATURE:
<223> OTHER INFORMATION: linker

<400> SEQUENCE: 24

Pro Arg Asn Ser Ile His Phe Leu His Pro Leu Leu Val Ala Pro Leu
1               5                   10                  15

Gly Ala

<210> SEQ ID NO 25
<211> LENGTH: 18
<212> TYPE: PRT
<213> ORGANISM: Artificial
<220> FEATURE:
<223> OTHER INFORMATION: linker

<400> SEQUENCE: 25

Met Pro Ser Leu Ser Gly Val Leu Gln Val Arg Tyr Leu Ser Pro Pro
1               5                   10                  15

Asp Leu

<210> SEQ ID NO 26
<211> LENGTH: 18
<212> TYPE: PRT
<213> ORGANISM: Artificial
<220> FEATURE:
<223> OTHER INFORMATION: linker

<400> SEQUENCE: 26

Ser Pro Gln Tyr Pro Ser Pro Leu Thr Leu Thr Leu Pro Pro His Pro
1               5                   10                  15

Ser Leu

```
<210> SEQ ID NO 27
<211> LENGTH: 18
<212> TYPE: PRT
<213> ORGANISM: Artificial
<220> FEATURE:
<223> OTHER INFORMATION: linker

<400> SEQUENCE: 27

Asn Pro Ser Leu Asn Pro Pro Ser Tyr Leu His Arg Ala Pro Ser Arg
1               5                   10                  15

Ile Ser

<210> SEQ ID NO 28
<211> LENGTH: 17
<212> TYPE: PRT
<213> ORGANISM: Artificial
<220> FEATURE:
<223> OTHER INFORMATION: linker

<400> SEQUENCE: 28

Leu Pro Trp Arg Thr Ser Leu Leu Pro Ser Leu Pro Leu Arg Arg Arg
1               5                   10                  15

Pro

<210> SEQ ID NO 29
<211> LENGTH: 18
<212> TYPE: PRT
<213> ORGANISM: Artificial
<220> FEATURE:
<223> OTHER INFORMATION: linker

<400> SEQUENCE: 29

Pro Pro Leu Phe Ala Lys Gly Pro Val Gly Leu Leu Ser Arg Ser Phe
1               5                   10                  15

Pro Pro

<210> SEQ ID NO 30
<211> LENGTH: 18
<212> TYPE: PRT
<213> ORGANISM: Artificial
<220> FEATURE:
<223> OTHER INFORMATION: linker

<400> SEQUENCE: 30

Val Pro Pro Ala Pro Val Val Ser Leu Arg Ser Ala His Ala Arg Pro
1               5                   10                  15

Pro Tyr

<210> SEQ ID NO 31
<211> LENGTH: 17
<212> TYPE: PRT
<213> ORGANISM: Artificial
<220> FEATURE:
<223> OTHER INFORMATION: linker

<400> SEQUENCE: 31

Leu Arg Pro Thr Pro Pro Arg Val Arg Ser Tyr Thr Cys Cys Pro Thr
1               5                   10                  15

Pro

<210> SEQ ID NO 32
<211> LENGTH: 18
<212> TYPE: PRT
```

<213> ORGANISM: Artificial
<220> FEATURE:
<223> OTHER INFORMATION: linker

<400> SEQUENCE: 32

Pro Asn Val Ala His Val Leu Pro Leu Leu Thr Val Pro Trp Asp Asn
1               5                   10                  15

Leu Arg

<210> SEQ ID NO 33
<211> LENGTH: 18
<212> TYPE: PRT
<213> ORGANISM: Artificial
<220> FEATURE:
<223> OTHER INFORMATION: linker

<400> SEQUENCE: 33

Cys Asn Pro Leu Leu Pro Leu Cys Ala Arg Ser Pro Ala Val Arg Thr
1               5                   10                  15

Phe Pro

<210> SEQ ID NO 34
<211> LENGTH: 11
<212> TYPE: PRT
<213> ORGANISM: Artificial
<220> FEATURE:
<223> OTHER INFORMATION: linker

<400> SEQUENCE: 34

Gly Ala Pro Ala Pro Ala Ala Pro Ala Pro Ala
1               5                   10

<210> SEQ ID NO 35
<211> LENGTH: 4
<212> TYPE: PRT
<213> ORGANISM: Artificial
<220> FEATURE:
<223> OTHER INFORMATION: linker

<400> SEQUENCE: 35

Pro Pro Pro Pro
1

<210> SEQ ID NO 36
<211> LENGTH: 8
<212> TYPE: PRT
<213> ORGANISM: Artificial
<220> FEATURE:
<223> OTHER INFORMATION: linker

<400> SEQUENCE: 36

Asp Lys Thr His Thr Cys Ala Ala
1               5

<210> SEQ ID NO 37
<211> LENGTH: 11
<212> TYPE: PRT
<213> ORGANISM: Artificial
<220> FEATURE:
<223> OTHER INFORMATION: linker

<400> SEQUENCE: 37

Asp Lys Thr His Thr Cys Pro Pro Cys Pro Ala
1               5                   10

```
<210> SEQ ID NO 38
<211> LENGTH: 18
<212> TYPE: PRT
<213> ORGANISM: Artificial
<220> FEATURE:
<223> OTHER INFORMATION: linker

<400> SEQUENCE: 38

Asp Lys Thr His Thr Cys Pro Pro Cys Pro Ala Thr Cys Pro Pro Cys
1               5                   10                  15

Pro Ala

<210> SEQ ID NO 39
<211> LENGTH: 25
<212> TYPE: PRT
<213> ORGANISM: Artificial
<220> FEATURE:
<223> OTHER INFORMATION: linker

<400> SEQUENCE: 39

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 40
<211> LENGTH: 30
<212> TYPE: PRT
<213> ORGANISM: Artificial
<220> FEATURE:
<223> OTHER INFORMATION: linker

<400> SEQUENCE: 40

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 41
<211> LENGTH: 31
<212> TYPE: PRT
<213> ORGANISM: Artificial
<220> FEATURE:
<223> OTHER INFORMATION: linker

<400> SEQUENCE: 41

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 42
<211> LENGTH: 15
<212> TYPE: PRT
<213> ORGANISM: Artificial
<220> FEATURE:
<223> OTHER INFORMATION: linker

<400> SEQUENCE: 42

Asp Lys Thr His Thr Cys Cys Val Glu Cys Pro Pro Cys Pro Ala
1               5                   10                  15

<210> SEQ ID NO 43
<211> LENGTH: 26
<212> TYPE: PRT
```

```
<213> ORGANISM: Artificial
<220> FEATURE:
<223> OTHER INFORMATION: linker

<400> SEQUENCE: 43

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 44
<211> LENGTH: 11
<212> TYPE: PRT
<213> ORGANISM: Artificial
<220> FEATURE:
<223> OTHER INFORMATION: linker

<400> SEQUENCE: 44

Asp Lys Thr His Thr Cys Pro Ser Cys Pro Ala
1               5                   10

<210> SEQ ID NO 45
<211> LENGTH: 10
<212> TYPE: PRT
<213> ORGANISM: Artificial
<220> FEATURE:
<223> OTHER INFORMATION: linker

<400> SEQUENCE: 45

Gly Gly Gly Gly Ser Gly Gly Gly Gly Ser
1               5                   10

<210> SEQ ID NO 46
<211> LENGTH: 15
<212> TYPE: PRT
<213> ORGANISM: Artificial
<220> FEATURE:
<223> OTHER INFORMATION: linker

<400> SEQUENCE: 46

Gly Gly Gly Gly Ser Gly Gly Gly Gly Ser Gly Gly Gly Gly Ser
1               5                   10                  15

<210> SEQ ID NO 47
<211> LENGTH: 20
<212> TYPE: PRT
<213> ORGANISM: Artificial
<220> FEATURE:
<223> OTHER INFORMATION: linker

<400> SEQUENCE: 47

Gly Gly Gly Gly Ser Gly Gly Gly Gly Ser Gly Gly Gly Gly Ser Gly
1               5                   10                  15

Gly Gly Gly Ser
            20

<210> SEQ ID NO 48
<211> LENGTH: 25
<212> TYPE: PRT
<213> ORGANISM: Artificial
<220> FEATURE:
<223> OTHER INFORMATION: linker

<400> SEQUENCE: 48

Gly Gly Gly Gly Ser Gly Gly Gly Gly Ser Gly Gly Gly Gly Ser Gly
1               5                   10                  15
```

```
Gly Gly Gly Ser Gly Gly Gly Gly Ser
            20                  25

<210> SEQ ID NO 49
<211> LENGTH: 21
<212> TYPE: PRT
<213> ORGANISM: Artificial
<220> FEATURE:
<223> OTHER INFORMATION: linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 49

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 50
<211> LENGTH: 26
<212> TYPE: PRT
<213> ORGANISM: Artificial
<220> FEATURE:
<223> OTHER INFORMATION: linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 50

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 51
<211> LENGTH: 31
<212> TYPE: PRT
<213> ORGANISM: Artificial
<220> FEATURE:
<223> OTHER INFORMATION: linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
```

<400> SEQUENCE: 51

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 52
<211> LENGTH: 119
<212> TYPE: PRT
<213> ORGANISM: Artificial
<220> FEATURE:
<223> OTHER INFORMATION: dAbH1

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Ser Thr Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115

<210> SEQ ID NO 53
<211> LENGTH: 110
<212> TYPE: PRT
<213> ORGANISM: Artificial
<220> FEATURE:
<223> OTHER INFORMATION: dAbL1

<400> SEQUENCE: 53

Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Lys
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Gly Gly Thr Lys Val Glu Ile Lys
            100                 105                 110

<210> SEQ ID NO 54
<211> LENGTH: 120
<212> TYPE: PRT
<213> ORGANISM: Artificial

```
<220> FEATURE:
<223> OTHER INFORMATION: dAbH2

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Arg Tyr
            20                  25                  30

Ala Met Thr Trp Val Arg Gln Ala Pro Gly Lys Gly Leu Glu Trp Ile
        35                  40                  45

Gly Thr Ile Thr Thr Gly Gly Asn Thr Asn Tyr Ala Asn Trp Ala Lys
    50                  55                  60

Gly Arg Phe Thr Ile Ser Lys Asp Ser Thr Thr Val Tyr Leu Gln Met
65                  70                  75                  80

Asn Ser Leu Arg Ala Glu Asp Thr Ala Val Tyr Tyr Cys Ala Arg Gly
                85                  90                  95

Gly Tyr Val Ser Tyr Ala Asp Ala Thr Glu Leu Ser Leu Trp Gly Gln
            100                 105                 110

Gly Thr Leu Val Thr Val Ser Ser
        115                 120

<210> SEQ ID NO 55
<211> LENGTH: 110
<212> TYPE: PRT
<213> ORGANISM: Artificial
<220> FEATURE:
<223> OTHER INFORMATION: dAbL2

<400> SEQUENCE: 55

Asp Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Ser Arg
            20                  25                  30

Leu Ala Trp Tyr Gln Gln Lys Pro Gly Lys Ala Pro Lys Leu Leu Ile
        35                  40                  45

Tyr Tyr Ala Ser Thr Val Ala Ser Gly Val Pro Ser Arg Phe Lys Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asp Tyr Ser Ser Ser
                85                  90                  95

Ser Ser Tyr Ala Phe Gly Gly Gly Thr Lys Val Glu Ile Lys
            100                 105                 110

<210> SEQ ID NO 56
<211> LENGTH: 10
<212> TYPE: PRT
<213> ORGANISM: Artificial
<220> FEATURE:
<223> OTHER INFORMATION: CDRH1 dAbH1

<400> SEQUENCE: 56

Gly Ile Asp Leu Ser Asn Tyr Ala Ile Asn
1               5                   10

<210> SEQ ID NO 57
<211> LENGTH: 16
<212> TYPE: PRT
<213> ORGANISM: Artificial
<220> FEATURE:
```

<223> OTHER INFORMATION: CDRH2 dAbH1

<400> SEQUENCE: 57

Ile Ile Trp Ala Ser Gly Thr Thr Phe Tyr Ala Thr Trp Ala Lys Gly
1               5                   10                  15

<210> SEQ ID NO 58
<211> LENGTH: 13
<212> TYPE: PRT
<213> ORGANISM: Artificial
<220> FEATURE:
<223> OTHER INFORMATION: CDRH3 dAbH1

<400> SEQUENCE: 58

Thr Val Pro Gly Tyr Ser Thr Ala Pro Tyr Phe Asp Leu
1               5                   10

<210> SEQ ID NO 59
<211> LENGTH: 12
<212> TYPE: PRT
<213> ORGANISM: Artificial
<220> FEATURE:
<223> OTHER INFORMATION: CDRL1 dAbL1

<400> SEQUENCE: 59

Gln Ser Ser Pro Ser Val Trp Ser Asn Phe Leu Ser
1               5                   10

<210> SEQ ID NO 60
<211> LENGTH: 7
<212> TYPE: PRT
<213> ORGANISM: Artificial
<220> FEATURE:
<223> OTHER INFORMATION: CDRL2 dAbL1

<400> SEQUENCE: 60

Glu Ala Ser Lys Leu Thr Ser
1               5

<210> SEQ ID NO 61
<211> LENGTH: 11
<212> TYPE: PRT
<213> ORGANISM: Artificial
<220> FEATURE:
<223> OTHER INFORMATION: CDRL3 dAbL1

<400> SEQUENCE: 61

Gly Gly Gly Tyr Ser Ser Ile Ser Asp Thr Thr
1               5                   10

<210> SEQ ID NO 62
<211> LENGTH: 10
<212> TYPE: PRT
<213> ORGANISM: Artificial
<220> FEATURE:
<223> OTHER INFORMATION: CDRH1 dAbH2

<400> SEQUENCE: 62

Gly Phe Ser Leu Ser Arg Tyr Ala Met Thr
1               5                   10

<210> SEQ ID NO 63
<211> LENGTH: 16
<212> TYPE: PRT
<213> ORGANISM: Artificial
<220> FEATURE:
<223> OTHER INFORMATION: CDRH2 dAbH2

```
<400> SEQUENCE: 63

Thr Ile Thr Thr Gly Gly Asn Thr Asn Tyr Ala Asn Trp Ala Lys Gly
1               5                   10                  15

<210> SEQ ID NO 64
<211> LENGTH: 14
<212> TYPE: PRT
<213> ORGANISM: Artificial
<220> FEATURE:
<223> OTHER INFORMATION: CDRH3 dAbH2

<400> SEQUENCE: 64

Gly Gly Tyr Val Ser Tyr Ala Asp Ala Thr Glu Leu Ser Leu
1               5                   10

<210> SEQ ID NO 65
<211> LENGTH: 11
<212> TYPE: PRT
<213> ORGANISM: Artificial
<220> FEATURE:
<223> OTHER INFORMATION: CDRL1 dAbL2

<400> SEQUENCE: 65

Gln Ala Ser Gln Ser Ile Gly Ser Arg Leu Ala
1               5                   10

<210> SEQ ID NO 66
<211> LENGTH: 7
<212> TYPE: PRT
<213> ORGANISM: Artificial
<220> FEATURE:
<223> OTHER INFORMATION: CDRL2 dAbL2

<400> SEQUENCE: 66

Tyr Ala Ser Thr Val Ala Ser
1               5

<210> SEQ ID NO 67
<211> LENGTH: 12
<212> TYPE: PRT
<213> ORGANISM: Artificial
<220> FEATURE:
<223> OTHER INFORMATION: CDRL3 dAbL2

<400> SEQUENCE: 67

Gln Ser Tyr Asp Tyr Ser Ser Ser Ser Ser Tyr Ala
1               5                   10

<210> SEQ ID NO 68
<211> LENGTH: 232
<212> TYPE: PRT
<213> ORGANISM: Artificial
<220> FEATURE:
<223> OTHER INFORMATION: CH1-dAbH1

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Gly Gly Gly Ser Gly Gly Gly Gly
            100                 105                 110

Ser Glu Val Gln Leu Leu Glu Ser Gly Gly Leu Val Gln Pro Gly
            115                 120                 125

Gly Ser Leu Arg Leu Ser Cys Ala Val Ser Gly Ile Asp Leu Ser Asn
130                 135                 140

Tyr Ala Ile Asn Trp Val Arg Gln Ala Pro Gly Lys Gly Leu Glu Trp
145                 150                 155                 160

Ile Gly Ile Ile Trp Ala Ser Gly Thr Thr Phe Tyr Ala Thr Trp Ala
                165                 170                 175

Lys Gly Arg Phe Thr Ile Ser Arg Asp Ser Thr Thr Val Tyr Leu Gln
            180                 185                 190

Met Asn Ser Leu Arg Ala Glu Asp Thr Ala Val Tyr Tyr Cys Ala Arg
            195                 200                 205

Thr Val Pro Gly Tyr Ser Thr Ala Pro Tyr Phe Asp Leu Trp Gly Gln
    210                 215                 220

Gly Thr Leu Val Thr Val Ser Ser
225                 230

<210> SEQ ID NO 69
<211> LENGTH: 233
<212> TYPE: PRT
<213> ORGANISM: Artificial
<220> FEATURE:
<223> OTHER INFORMATION: CH1-dAbH2

<400> SEQUENCE: 69

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Gly Gly Gly Ser Gly Gly Gly Gly
            100                 105                 110

Ser Glu Val Gln Leu Val Glu Ser Gly Gly Leu Val Gln Pro Gly
            115                 120                 125

Gly Ser Leu Arg Leu Ser Cys Ala Val Ser Gly Phe Ser Leu Ser Arg
130                 135                 140

Tyr Ala Met Thr Trp Val Arg Gln Ala Pro Gly Lys Gly Leu Glu Trp
145                 150                 155                 160

Ile Gly Thr Ile Thr Gly Gly Asn Thr Asn Tyr Ala Asn Trp Ala
                165                 170                 175

Lys Gly Arg Phe Thr Ile Ser Lys Asp Ser Thr Thr Val Tyr Leu Gln
            180                 185                 190
```

Met Asn Ser Leu Arg Ala Glu Asp Thr Ala Val Tyr Tyr Cys Ala Arg
        195                 200                 205

Gly Gly Tyr Val Ser Tyr Ala Asp Ala Thr Glu Leu Ser Leu Trp Gly
    210                 215                 220

Gln Gly Thr Leu Val Thr Val Ser Ser
225                 230

<210> SEQ ID NO 70
<211> LENGTH: 223
<212> TYPE: PRT
<213> ORGANISM: Artificial
<220> FEATURE:
<223> OTHER INFORMATION: CH1-dAbL1

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Gly Gly Gly Ser Gly Gly Gly Gly
            100                 105                 110

Ser Asp Ile Val Met Thr Gln Ser Pro Ser Ser Val Ser Ala Ser Val
        115                 120                 125

Gly Asp Arg Val Thr Ile Thr Cys Gln Ser Ser Pro Ser Val Trp Ser
    130                 135                 140

Asn Phe Leu Ser Trp Tyr Gln Gln Lys Pro Gly Lys Ala Pro Lys Leu
145                 150                 155                 160

Leu Ile Tyr Glu Ala Ser Lys Leu Thr Ser Gly Val Pro Ser Arg Phe
                165                 170                 175

Lys Gly Ser Gly Ser Gly Thr Phe Thr Leu Thr Ile Ser Ser Leu
            180                 185                 190

Gln Pro Glu Asp Phe Ala Thr Tyr Tyr Cys Gly Gly Gly Tyr Ser Ser
        195                 200                 205

Ile Ser Asp Thr Thr Phe Gly Gly Gly Thr Lys Val Glu Ile Lys
    210                 215                 220

<210> SEQ ID NO 71
<211> LENGTH: 223
<212> TYPE: PRT
<213> ORGANISM: Artificial
<220> FEATURE:
<223> OTHER INFORMATION: CH1-dAbL2

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Gly Gly Gly Ser Gly Gly Gly Gly
            100                 105                 110

Ser Asp Ile Val Met Thr Gln Ser Pro Ser Thr Leu Ser Ala Ser Val
            115                 120                 125

Gly Asp Arg Val Thr Ile Thr Cys Gln Ala Ser Gln Ser Ile Gly Ser
            130                 135                 140

Arg Leu Ala Trp Tyr Gln Gln Lys Pro Gly Lys Ala Pro Lys Leu Leu
145                 150                 155                 160

Ile Tyr Tyr Ala Ser Thr Val Ala Ser Gly Val Pro Ser Arg Phe Lys
                165                 170                 175

Gly Ser Gly Ser Gly Thr Glu Phe Thr Leu Thr Ile Ser Ser Leu Gln
            180                 185                 190

Pro Asp Asp Phe Ala Thr Tyr Tyr Cys Gln Ser Tyr Asp Tyr Ser Ser
            195                 200                 205

Ser Ser Ser Tyr Ala Phe Gly Gly Gly Thr Lys Val Glu Ile Lys
            210                 215                 220
```

<210> SEQ ID NO 72
<211> LENGTH: 227
<212> TYPE: PRT
<213> ORGANISM: Artificial
<220> FEATURE:
<223> OTHER INFORMATION: Ck1-dAbL1

<400> SEQUENCE: 72

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys Gly Gly Gly Gly Ser
            100                 105                 110

Gly Gly Gly Gly Ser Asp Ile Val Met Thr Gln Ser Pro Ser Ser Val
            115                 120                 125

Ser Ala Ser Val Gly Asp Arg Val Thr Ile Thr Cys Gln Ser Ser Pro
            130                 135                 140

Ser Val Trp Ser Asn Phe Leu Ser Trp Tyr Gln Gln Lys Pro Gly Lys
145                 150                 155                 160

Ala Pro Lys Leu Leu Ile Tyr Glu Ala Ser Lys Leu Thr Ser Gly Val
                165                 170                 175

Pro Ser Arg Phe Lys Gly Ser Gly Ser Gly Thr Asp Phe Thr Leu Thr
```

```
                 180                 185                 190
Ile Ser Ser Leu Gln Pro Glu Asp Phe Ala Thr Tyr Tyr Cys Gly Gly
            195                 200                 205

Gly Tyr Ser Ser Ile Ser Asp Thr Thr Phe Gly Gly Gly Thr Lys Val
    210                 215                 220

Glu Ile Lys
225

<210> SEQ ID NO 73
<211> LENGTH: 227
<212> TYPE: PRT
<213> ORGANISM: Artificial
<220> FEATURE:
<223> OTHER INFORMATION: Ck1-dAbL2

<400> SEQUENCE: 73

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys Gly Gly Gly Gly Ser
            100                 105                 110

Gly Gly Gly Gly Ser Asp Ile Val Met Thr Gln Ser Pro Ser Thr Leu
        115                 120                 125

Ser Ala Ser Val Gly Asp Arg Val Thr Ile Thr Cys Gln Ala Ser Gln
    130                 135                 140

Ser Ile Gly Ser Arg Leu Ala Trp Tyr Gln Gln Lys Pro Gly Lys Ala
145                 150                 155                 160

Pro Lys Leu Leu Ile Tyr Tyr Ala Ser Thr Val Ala Ser Gly Val Pro
                165                 170                 175

Ser Arg Phe Lys Gly Ser Gly Ser Gly Thr Glu Phe Thr Leu Thr Ile
            180                 185                 190

Ser Ser Leu Gln Pro Asp Asp Phe Ala Thr Tyr Tyr Cys Gln Ser Tyr
        195                 200                 205

Asp Tyr Ser Ser Ser Ser Tyr Ala Phe Gly Gly Gly Thr Lys Val
    210                 215                 220

Glu Ile Lys
225

<210> SEQ ID NO 74
<211> LENGTH: 255
<212> TYPE: PRT
<213> ORGANISM: Artificial
<220> FEATURE:
<223> OTHER INFORMATION: Fab' A heavy chain

<400> SEQUENCE: 74

Met Lys Lys Thr Ala Ile Ala Ile Ala Val Ala Leu Ala Gly Phe Ala
1               5                   10                  15
```

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Phe Ser Gly Phe
        35                  40                  45

Ser Leu Ser Thr Ser Gly Val Gly Val Gly Trp Val Arg Gln Ala Pro
    50                  55                  60

Gly Lys Gly Leu Glu Trp Val Ala His Ile Trp Trp Asp Gly Asp Glu
65                  70                  75                  80

Ser Tyr Asn Pro Ser Leu Lys Thr Gln Phe Thr Ile Ser Lys Asp Thr
                85                  90                  95

Ser Lys Asn Thr Val Tyr Leu Gln Met Asn Ser Leu Arg Ala Glu Asp
            100                 105                 110

Thr Ala Val Tyr Tyr Cys Ala Arg Asn Arg Tyr Asp Pro Pro Trp Phe
        115                 120                 125

Val Asp Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Thr Cys Asp Lys Thr His Thr Cys Pro Pro Cys Pro Ala
                245                 250                 255

<210> SEQ ID NO 75
<211> LENGTH: 235
<212> TYPE: PRT
<213> ORGANISM: Artificial
<220> FEATURE:
<223> OTHER INFORMATION: Fab A light chain

<400> SEQUENCE: 75

Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Asn Tyr Leu Ser Trp Tyr Gln Gln Lys Pro Gly Lys Ala
    50                  55                  60

Pro Lys Leu Leu Ile Tyr Tyr Thr Ser Lys Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Phe Ala Thr Tyr Tyr Cys Gln Gln Gly
            100                 105                 110

Lys Met Leu Pro Trp Thr Phe Gly Gln Gly Thr Lys Val Glu Ile Lys
        115                 120                 125

```
Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Val Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 76
<211> LENGTH: 250
<212> TYPE: PRT
<213> ORGANISM: Artificial
<220> FEATURE:
<223> OTHER INFORMATION: Fab'A heavy chain altered hinge

<400> SEQUENCE: 76

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
                20                  25                  30

Val Gln Pro Gly Gly Ser Leu Arg Leu Ser Cys Ala Phe Ser Gly Phe
            35                  40                  45

Ser Leu Ser Thr Ser Gly Val Gly Val Gly Trp Val Arg Gln Ala Pro
50                  55                  60

Gly Lys Gly Leu Glu Trp Val Ala His Ile Trp Trp Asp Gly Asp Glu
65                  70                  75                  80

Ser Tyr Asn Pro Ser Leu Lys Thr Gln Phe Thr Ile Ser Lys Asp Thr
                85                  90                  95

Ser Lys Asn Thr Val Tyr Leu Gln Met Asn Ser Leu Arg Ala Glu Asp
                100                 105                 110

Thr Ala Val Tyr Tyr Cys Ala Arg Asn Arg Tyr Asp Pro Pro Trp Phe
            115                 120                 125

Val Asp Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Thr Cys Asp Lys Thr His Thr Ser
                245                 250
```

<210> SEQ ID NO 77
<211> LENGTH: 244
<212> TYPE: PRT
<213> ORGANISM: Artificial
<220> FEATURE:
<223> OTHER INFORMATION: Fab A heavy chain

<400> SEQUENCE: 77

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Phe Ser Gly Phe
        35                  40                  45

Ser Leu Ser Thr Ser Gly Val Gly Val Gly Trp Val Arg Gln Ala Pro
    50                  55                  60

Gly Lys Gly Leu Glu Trp Val Ala His Ile Trp Trp Asp Gly Asp Glu
65                  70                  75                  80

Ser Tyr Asn Pro Ser Leu Lys Thr Gln Phe Thr Ile Ser Lys Asp Thr
                85                  90                  95

Ser Lys Asn Thr Val Tyr Leu Gln Met Asn Ser Leu Arg Ala Glu Asp
            100                 105                 110

Thr Ala Val Tyr Tyr Cys Ala Arg Asn Arg Tyr Asp Pro Pro Trp Phe
        115                 120                 125

Val Asp Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Thr Cys
```

DUAL SPECIFICITY ANTIBODY FUSIONS

The present invention relates to new dual specificity antibody fusion proteins. Such antibodies comprise a first specificity to an antigen of interest, and a second specificity for a second antigen of interest, for example a serum carrier protein for use in extending their in vivo serum half-life. Methods for the production of such molecules and pharmaceutical compositions comprising them are also provided.

The high specificity and affinity of antibodies makes them ideal diagnostic and therapeutic agents, particularly for modulating protein:protein interactions. Advances in the field of recombinant antibody technology have resulted in the production of antibody fragments, such as Fv, Fab, Fab' and F(ab')$_2$ fragments and other antibody fragments. These smaller molecules retain the antigen binding activity of whole antibodies and can also exhibit improved tissue penetration and pharmacokinetic properties in comparison to whole immunoglobulin molecules. Indeed, antibody fragments are proving to be versatile therapeutic agents, as seen by the recent success of products such as ReoPro® and Lucentis®. Whilst such fragments appear to exhibit a number of advantages over whole immunoglobulins, they also suffer from an increased rate of clearance from serum since they lack the Fc domain that imparts a long lifetime in vivo (Medasan et al., 1997, J. Immunol. 158:2211-2217).

Antibodies with dual specificity, i.e. which bind to two different antigens have been previously described (for reviews, see Segal et al., 1999, Curr. Opin. Immunol. 11:558-562; Plückthun & Pack, 1997, Immunotechnology, 3:83-105; Fischer and Leger, 2007, Pathobiology, 74, 3-14). Dual specificity antibodies are also described in WO02/02773, US2007065440, US2006257406, US2006106203 and US2006280734. Previous approaches to making heterobispecific antibody-based molecules have generally employed chemical cross-linking or protein engineering techniques. Chemical cross-linking suffers from poor yields of hetero- and homo-dimer formation and the requirement for their subsequent chromatographic separation. Protein engineering approaches have either been highly elaborate (e.g. knobs-into-holes engineering; Ridgway et al., 1996, Protein Eng. 9(7):617-621) or have used molecules with inappropriate stability characteristics (e.g. diabodies, scFv). In some cases bispecific antibodies can also suffer from steric hindrance problems such that both antigens cannot bind simultaneously to each antibody arm.

Single variable domain antibodies also known as single domain antibodies or dAbs, correspond to the variable regions of either the heavy (VH) or light (VL) chain of an antibody. Murine single-domain antibodies were described by Ward et al., 1989, Nature, 341, 544-546. Human and 'camelised' human single domain antibodies have also been described (Holt et al., 2003, *Trends in Biotechnology*, 21, 484-490). Single domain antibodies have also been obtained from the camelids (camels and llamas) and cartilaginous fish (wobbegong and nurse sharks). These organisms have evolved high affinity single V-like domains (called VhH in camelids and V-NAR in sharks), mounted on an Fc-equivalent constant domain framework as an integral and crucial component of their immune system (see Holliger & Hudson, for a review; 2005, Nature Biotechnology, 23(9):1126-1136).

Single domain antibody-enzyme fusions have been described in EP0368684. Single domain-effector group fusions have also been described in WO2004/058820 which comprise a single variable domain. Dual variable domain immunoglobulins have been described in WO2007/024715. Dual specific ligands comprising two single domain antibodies with differing specificities have been described in EP 1517921.

Means to improve the half-life of antibody fragments, such as Fv, Fab, Fab', F(ab')$_2$ and other antibody fragments, are known. One approach has been to conjugate the fragment to polymer molecules. Thus, the short circulating half-life of Fab', F(ab')$_2$ fragments in animals has been improved by conjugation to polyethylene glycol (PEG; see, for example, WO98/25791, WO99/64460 and WO98/37200). Another approach has been to modify the antibody fragment by conjugation to an agent that interacts with the FcRn receptor (see, for example, WO97/34631). Yet another approach to extend half-life has been to use polypeptides that bind serum albumin (see, for example, Smith et al., 2001, Bioconjugate Chem. 12:750-756; EP0486525; U.S. Pat. No. 6,267,964; WO04/001064; WO02/076489; and WO01/45746). However, there still remains a need to produce antigen-binding immunoglobulin proteins that have a long in vivo half-life, as an alternative to those that have a long half life because they interact with the FcRn receptor, without being chemically modified by conjugation to PEG, or being conjugated to human serum albumin.

A variety of proteins exist in plasma and include thyroxine-binding protein, transthyretin, α1-acid glycoprotein, transferrin, fibrinogen and albumin, or a fragment of any thereof. Serum carrier proteins circulate within the body with half-lives measured in days, for example, 5 days for thyroxine-binding protein or 2 days for transthyretin (Bartalena & Robbins, 1993, Clinics in Lab. Med. 13:583-598), or 65 hours in the second phase of turnover of iodinated α1-acid glycoprotein (Bree et al., 1986, Clin. Pharmacokin. 11:336-342). Data from Gitlin et al. (1964, J. Clin. Invest. 10:1938-1951) suggest that in pregnant women, the half-life of α1-acid glycoprotein is 3.8 days, 12 days for transferrin and 2.5 days for fibrinogen. Serum albumin is an abundant protein in both vascular and extravascular compartments with a half-life in man of about 19 days (Peters, 1985, Adv Protein Chem. 37:161-245). This is similar to the half-life of IgG1, which is about 21 days (Waldeman & Strober, 1969, Progr. Allergy, 13:1-110).

The present invention provides improved dual specificity antibody fusion proteins which can be produced recombinantly and are capable of binding two antigens simultaneously.

Thus, the present invention provides dual specificity antibody fusion proteins which comprise an immunoglobulin moiety with a first specificity for an antigen of interest, and further comprise a single domain antibody (dAb) with specificity for a second antigen of interest.

The present invention also provides dual specificity antibody fusion proteins which comprise an immunoglobulin moiety with a first specificity for an antigen of interest, and further comprise at least one single domain antibody with specificity for a second antigen of interest.

A dual specificity antibody fusion of the invention will be capable of selectively binding to two antigens of interest.

In one embodiment, an antigen of interest bound by the Fab or Fab' fragment may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD134 (OX40), ICOS, BCMP7, CD137, CD27L, CDCP1, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof.

Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody fusion protein of the invention may be used to functionally alter the activity of the antigen of interest. For example, the antibody fusion protein may neutralize, antagonize or agonise the activity of said antigen, directly or indirectly.

In one embodiment, a second antigen of interest bound by the single domain antibody or antibodies in the dual specificity antibody fusion proteins of the invention may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD134 (OX40), ICOS, BCMP7, CD137, CD27L, CDCP1, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof.

Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon 13 or interferon α, tumour necrosis factor-α, tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

Other antigens which may be bound by the single domain antibody or antibodies include serum carrier proteins, polypeptides which enable cell-mediated effector function recruitment and nuclide chelator proteins.

Thus, in one example the present invention provides dual specificity antibody fusion proteins which comprise an immunoglobulin moiety with a first specificity for an antigen of interest, and further comprise a single domain antibody with specificity for a second protein, the latter providing the ability to recruit effector functions, such as complement pathway activation and/or effector cell recruitment. Further, fusion proteins of the present invention may be used to chelate radionuclides by virtue of a single domain antibody which binds to a nuclide chelator protein. Such fusion proteins are of use in imaging or radionuclide targeting approaches to therapy.

Accordingly, in one example there is provided an isolated dual specificity antibody fusion protein comprising an antibody Fab or Fab' fragment with specificity for an antigen of interest, said fragment being fused to at least one dAb which has specificity for a recruitment polypeptide, said dAb providing the ability to recruit cell-mediated effector function(s), directly or indirectly, by binding to said recruitment polypeptide.

The recruitment of effector function may be direct in that effector function is associated with a cell, said cell bearing a recruitment molecule on its surface. Indirect recruitment may occur when binding of a dAb to a recruitment molecule causes release of, for example, a factor which in turn may directly or indirectly recruit effector function, or may be via activation of a signalling pathway. Examples include TNFα, IL2, IL6, IL8, IL17, IFNγ, histamine, C1q, opsonin and other members of the classical and alternative complement activation cascades, such as C2, C4, C3-convertase, and C5 to C9.

As used herein, 'a recruitment polypeptide' includes a FcγR such as FcγRI, FcγRII and Fc γRIII, a complement pathway protein such as, but without limitation, C1q and C3, a CD marker protein (Cluster of Differentiation marker) such as, but without limitation, CD68, CD115, CD16, CD80, CD83, CD86, CD56, CD64, CD3, CD4, CD8, CD28, CD45, CD19, CD20 and CD22. Further recruitment polypeptides which are CD marker proteins include CD1, CD1d, CD2, CD5, CD8, CD9, CD10, CD11, CD11a, CD11b, CD11c, CD13, CD14, CD15, CD16, CD18, CD19, CD20, CD21, CD22, CD23, CD24, CD25, CD26, CD27, CD28, CD29, CD30, CD31, CD32, CD33, CD34, CD35, CD36, CD37, CD38, CD40, CD43, CD44, CD45, CD46, CD49, CD49a, CD49b, CD49c, CD49d, CD52, CD53, CD54, CD55, CD56, CD58, CD59, CD61, CD62, D62E, CD62L, CD62P, CD63, CD64, CD66e, CD68, CD70, CD71, CD72, CD79, CD80, CD81, CD82, CD83, CD84, CD85, CD86, CD88, CD89, CD90, CD94, CD95, CD98, CD106, CD114, CD116, CD117, CD118, CD120, CD122, CD130, CD131, CD132, CD133, CD134, CD135, CD137, CD138, CD141, CD142, CD143, CD146, CD147, CD151, CD152, CD153, CD154, CD155, CD162, CD164, CD169, CD184, CD206, CD209, CD257, CD278, CD281, CD282, CD283 and CD304, or a fragment of any thereof which retains the ability to recruit cell-mediated effector function either directly or indirectly. A recruitment polypeptide also includes immunoglobulin molecules such as IgG1, IgG2, IgG3, IgG4, IgE and IgA which possess effector function.

In one embodiment, the second protein for which the dAb has specificity is a complement pathway protein, with C1q being particularly preferred.

In a preferred embodiment, the second protein for which the dAb has specificity is a CD marker protein, with CD68, CD80, CD86, CD64, CD3, CD4, CD8 CD45, CD16 and CD35 being particularly preferred.

Accordingly also provided is an isolated dual specificity antibody fusion protein comprising an antibody fragment with specificity for an antigen of interest, said fragment being fused to at least one dAb which has specificity for a CD molecule selected from the group consisting of CD68, CD80, CD86, CD64, CD3, CD4, CD8 CD45, CD16 and CD35.

In one embodiment the single domain antibody or antibodies provide an extended half-life to the immunoglobulin moiety with the first specificity.

Accordingly, in one embodiment there is provided a dual specificity antibody fusion protein comprising an antibody Fab or Fab' fragment with specificity for an antigen of interest, said fragment being fused to at least one single domain antibody which has specificity for a serum carrier protein, a circulating immunoglobulin molecule, or CD35/CR1, said single domain antibody providing an extended half-life to the antibody fragment with specificity for said antigen of interest by binding to said serum carrier protein, circulating immunoglobulin molecule or CD35/CR1.

In one embodiment there is provided an isolated dual specificity antibody fusion protein comprising an antibody Fab or Fab' fragment with specificity for an antigen of interest, said fragment being fused to at least one single domain antibody which has specificity for a serum carrier protein, a circulating immunoglobulin molecule, or CD35/CR1, said single domain antibody providing an extended half-life to the antibody fragment with specificity for said antigen of interest by binding to said serum carrier protein, circulating immunoglobulin molecule or CD35/CR1.

As used herein, 'serum carrier proteins' include thyroxine-binding protein, transthyretin, α1-acid glycoprotein, transferrin, fibrinogen and albumin, or a fragment of any thereof.

As used herein, a 'circulating immunoglobulin molecule' includes IgG1, IgG2, IgG3, IgG4, sIgA, IgM and IgD, or a fragment of any thereof.

CD35/CR1 is a protein present on red blood cells which have a half life of 36 days (normal range of 28 to 47 days; Lanaro et al., 1971, Cancer, 28(3):658-661).

In a preferred embodiment, the second protein for which the dAb has specificity is a serum carrier protein, with a human serum carrier protein being particularly preferred. In a most preferred embodiment, the serum carrier protein is human serum albumin.

Accordingly provided is a dual specificity antibody fusion protein comprising an antibody Fab or Fab' fragment with specificity for an antigen of interest, said fragment being fused to at least one single domain antibody which has specificity for human serum albumin.

In one embodiment the present invention provides an isolated dual specificity antibody fusion protein comprising an antibody Fab or Fab' fragment with specificity for an antigen of interest, said fragment being fused to at least one single domain antibody which has specificity for human serum albumin.

In one embodiment, the antibody fragment with specificity for an antigen of interest is a Fab fragment. In another embodiment, the antibody fragment with specificity for an antigen of interest is a Fab' fragment.

Thus, in one most preferred embodiment, the antibody fusion proteins of the invention are translation fusion proteins, i.e. genetic fusions, the sequence of each of which is encoded by an expression vector. Alternatively, the antibody fusion protein components have been fused using chemical means, i.e. by chemical conjugation or chemical cross-linking. Such chemical means are known in the art.

In one example, the antibody fragments are Fab' fragments which possess a native or a modified hinge region. Where the antibody fragment for use in preparing a dual specificity antibody fusion protein of the invention is a Fab' fragment, said fragment is generally extended at the C-terminus of the heavy chain by one or more amino acids. Thus, an antibody fusion of the invention can comprise a Fab' fragment translation fused (or chemically fused) to a dAb, directly or via a linker. Further, examples of suitable antibody Fab' fragments include those described in WO2005003170 and WO2005003171.

In another example, the antibody fragments are Fab fragments. Thus, an antibody fusion of the invention can comprise a Fab fragment translation fused (or chemically fused) to a linker sequence which in turn is translation fused (or chemically fused) to a dAb. Preferably, the Fab fragment is a Fab fragment which terminates at the interchain cysteines, as described in WO2005/003169.

The antibody Fab or Fab' fragments of use in the present invention can be from any species but are preferably derived from a monoclonal antibody, a human antibody, or are humanised fragments. An antibody fragment for use in the present invention can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human.

In one embodiment, the antibody Fab or Fab' fragment is a monoclonal, fully human, humanized or chimeric antibody fragment. In one embodiment the antibody Fab or Fab' fragments are fully human or humanised.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule (see, for example, U.S. Pat. No. 5,585,089).

The antibodies for use in the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., *Advances in Immunology*, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403, 484; 5,580,717; 5,427,908; 5,750,753; 5,821,047; 5,571, 698; 5,427,908; 5,516,637; 5,780,225; 5,658,727; 5,733, 743; and 5,969,108. Also, transgenic mice, or other organisms, including other mammals, may be used to generate humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 B1 and EPO463151 B1.

The antibody Fab or Fab' fragment starting material for use in the present invention may be obtained from any whole antibody, especially a whole monoclonal antibody, using any suitable enzymatic cleavage and/or digestion techniques, for example by treatment with pepsin. Alternatively, or in addition the antibody starting material may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein.

The antibody fragment starting material may be obtained from any species including for example mouse, rat, rabbit, hamster, camel, llama, goat or human. Parts of the antibody fragment may be obtained from more than one species, for example the antibody fragments may be chimeric. In one example, the constant regions are from one species and the variable regions from another. The antibody fragment starting material may also be modified. In another example, the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibody fragments are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In the present invention each single domain antibody fused to the Fab or Fab' fragment may linked directly or via a linker.

Examples of suitable linker regions for linking a dAb to a Fab or Fab' include, but are not limited to, flexible linker sequences and rigid linker sequences. Flexible linker sequences include those disclosed in Huston et al., 1988, PNAS 85:5879-5883; Wright & Deonarain, Mol. Immunol., 2007, 44(11):2860-2869; Alfthan et al., Prot. Eng., 1995, 8(7):725-731; Luo et al., J. Biochem., 1995, 118(4):825-831; Tang et al., 1996, J. Biol. Chem. 271(26):15682-15686; and Turner et al., 1997, JIMM 205, 42-54 (see Table 1 for representative examples).

TABLE 1

Flexible linker sequences

| SEQ ID NO: | SEQUENCE |
|---|---|
| 1 | SGGGGSE |
| 2 | DKTHTS |
| 3 | GGGGS |
| 45 | GGGGSGGGGS |
| 46 | GGGGSGGGGSGGGGS |
| 47 | GGGGSGGGGSGGGGSGGGGS |
| 48 | GGGGSGGGGSGGGGSGGGGSGGGGS |
| 4 | AAAGSG-GASAS |
| 5 | AAAGSG-XGGGS-GASAS |
| 49 | AAAGSG-XGGGSXGGGS -GASAS |
| 50 | AAAGSG- XGGGSXGGGSXGGGS -GASAS |
| 51 | AAAGSG- XGGGSXGGGSXGGGSXGGGS-GASAS |
| 6 | AAAGSG-XS-GASAS |
| 7 | PGGNRGTTTTRRPATTTGSSPGPTQSHY |
| 8 | ATTTGSSPGPT |
| 9 | ATTTGS |
| - | GS |
| 10 | EPSGPISTINSPPSKESHKSP |
| 11 | GTVAAPSVFIFPPSD |
| 12 | GGGGIAPSMVGGGGS |
| 13 | GGGGKVEGAGGGGGS |
| 14 | GGGGSMKSHDGGGGS |
| 15 | GGGGNLITIVGGGGS |
| 16 | GGGGVVPSLPGGGGS |
| 17 | GGEKSIPGGGGS |
| 18 | RPLSYRPPFPFGFPSVRP |
| 19 | YPRSIYIRRRHPSPSLTT |
| 20 | TPSHLSHILPSFGLPTFN |
| 21 | RPVSPFTFPRLSNSWLPA |
| 22 | SPAAHFPRSIPRPGPIRT |
| 23 | APGPSAPSHRSLPSRAFG |
| 24 | PRNSIHFLHPLLVAPLGA |
| 25 | MPSLSGVLQVRYLSPPDL |
| 26 | SPQYPSPLTLTLPPHPSL |
| 27 | NPSLNPPSYLHRAPSRIS |

TABLE 1-continued

Flexible linker sequences

| SEQ ID NO: | SEQUENCE |
|---|---|
| 28 | LPWRTSLLPSLPLRRRP |
| 29 | PPLFAKGPVGLLSRSFPP |
| 30 | VPPAPVVSLRSAHARPPY |
| 31 | LRPTPPRVRSYTCCPTP- |
| 32 | PNVAHVLPLLTVPWDNLR |
| 33 | CNPLLPLCARSPAVRTFP |

Examples of rigid linkers include the peptide sequences GAPAPAAPAPA (SEQ ID NO:34), PPPP (SEQ ID NO:35) and PPP.

In one embodiment, an antibody hinge sequence or part thereof is used as a linker, eg. the upper hinge sequence. Typically, antibody Fab' fragments for use in the present invention possess a native or a modified hinge region. Such hinge regions are used as a natural linker to the dAb moiety. The native hinge region is the hinge region normally associated with the $C_H1$ domain of the antibody molecule. A modified hinge region is any hinge that differs in length and/or composition from the native hinge region. Such hinges can include hinge regions from any other species, such as human, mouse, rat, rabbit, hamster, camel, llama or goat hinge regions. Other modified hinge regions may comprise a complete hinge region derived from an antibody of a different class or subclass from that of the $C_H1$ domain. Thus, for instance, a $C_H1$ domain of class γ1 may be attached to a hinge region of class γ4. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as alanine, or by converting suitably placed residues into cysteine residues. By such means the number of cysteine residues in the hinge region may be increased or decreased. In addition other characteristics of the hinge can be controlled, such as the distance of the hinge cysteine(s) from the light chain interchain cysteine, the distance between the cysteines of the hinge and the composition of other amino acids in the hinge that may affect properties of the hinge such as flexibility e.g. glycines may be incorporated into the hinge to increase rotational flexibility or prolines may be incorporated to reduce flexibility. Alternatively combinations of charged or hydrophobic residues may be incorporated into the hinge to confer multimerisation properties, see for example, Richter et al., 2001, Prot. Eng. 14(10):775-783 for use of charged or ionic tails, e.g., acidic tails as linkers and Kostelny et al., 1992, J. Immunol. 5(1):1547-1553 for leucine zipper sequences. Other modified hinge regions may be entirely synthetic and may be designed to possess desired properties such as length, composition and flexibility.

A number of modified hinge regions have already been described for example, in U.S. Pat. No. 5,677,425, U.S. Pat. No. 6,642,356, WO9915549, WO2005003170, WO2005003169, WO2005003170, WO9825971 and WO2005003171 and these are incorporated herein by reference. Such hinges generally follow on from the CH1 region, but may also be incorporated onto the end of constant region of a light chain kappa or lambda fragment; see Table 2 for examples.

TABLE 2

Hinge linker sequences

| SEQ ID NO: | SEQUENCE |
|---|---|
| 36 | DKTHTCAA |
| 37 | DKTHTCPPCPA |
| 38 | DKTHTCPPCPATCPPCPA |
| 39 | DKTHTCPPCPATCPPCPATCPPCPA |
| 40 | DKTHTCPPCPAGKPTLYNSLVMSDTAGTCY |
| 41 | DKTHTCPPCPAGKPTHVNVSVVMAEVDGTCY |
| 42 | DKTHTCCVECPPCPA |
| 43 | DKTHTCPRCPEPKSCDTPPPCPRCPA |
| 44 | DKTHTCPSCPA |

Single variable domains also known as single domain antibodies or dAbs for use in the present invention can be generated using methods known in the art and include those disclosed in WO2005118642, Ward et al., 1989, Nature, 341, 544-546 and Holt et al., 2003, Trends in Biotechnology, 21, 484-490. In one embodiment a single domain antibody for use in present invention is a heavy chain variable domain (VH) or a light chain domain (VL). Each light chain domain may be either of the kappa or lambda subgroup. Methods for isolating VH and VL domains have been described in the art, see for example EP0368684 and Ward et al., supra. Such domains may be derived from any suitable species or antibody starting material. In one embodiment the single domain antibody may be derived from a rodent, a human or other species. In one embodiment the single domain antibody is humanised.

In one embodiment the single domain antibody is derived from a phage display library, using the methods described in for example, WO2005/118642, Jespers et al., 2004, Nature Biotechnology, 22, 1161-1165 and Holt et al., 2003, Trends in Biotechnology, 21, 484-490. Preferably such single domain antibodies are fully human but may also be derived from other species. It will be appreciated that the sequence of the single domain antibody once isolated may be modified to improve the characteristics of the single domain antibody, for example solubility, as described in Holt et al., supra.

In one embodiment the dAb is a human sequence obtained from scFv phage-display or from a transgenic Humouse™ or Velocimouse™ or a humanised rodent.

In one embodiment, the dAb is obtained from a human or humanised rodent, a camelid or a shark. Such a dAb will preferably be humanised. In one example the single domain antibody is a VHH domain based on camelid immunoglobulins as described in EP0656946. In one example, a camel or a llama is immunised with an antigen of interest and blood collected when the titre is appropriate. The gene encoding the dAb may be cloned by single cell PCR, or the B cell(s) encoding the dAb may be immortalised by EBV transformation, or by fusion to an immortal cell line.

As described herein above, the present invention provides dual specificity antibody fusion proteins comprising an antibody Fab or Fab' fragment with specificity for an antigen of interest, said fragment being fused to at least one single domain antibody, directly or via a linker, which has specificity for a second antigen of interest.

Accordingly, in one embodiment, the antibody fragment, eg. Fab or Fab' fragment is fused at the N-terminus of the heavy or the light chain variable region to a dAb directly or via a linker. Alternatively, the antibody Fab or Fab' fragment is fused at the C-terminus of the heavy or light chain to a dAb directly or via a linker. In another embodiment the heavy and light chains of the antibody Fab or Fab' fragment are each fused at the C-terminus to a dAb directly or via a linker. The linkage can be a chemical conjugation but is most preferably a translation fusion, i.e. a genetic fusion where the sequence of each is encoded in sequence by an expression vector.

Typically the N-terminus of the single domain antibody will be fused to the C-terminus of the heavy or light chain of the Fab or Fab' fragment, directly or via a linker, and where the single domain antibody is fused to the N-terminus of the Fab or Fab' it will be fused via its C-terminus, optionally via a linker.

In one embodiment the present invention provides a dual specificity antibody fusion protein comprising or consisting of an antibody Fab or Fab' fragment with specificity for an antigen of interest, said fragment being fused to a single domain antibody at the N-terminus of the heavy or light chain which has specificity for a second antigen of interest.

In one embodiment the present invention provides a dual specificity antibody fusion protein comprising or consisting of an antibody Fab or Fab' fragment with specificity for an antigen of interest, said fragment being fused to a single domain antibody at the C-terminus of the heavy or light chain which has specificity for a second antigen of interest.

In one embodiment the present invention provides a dual specificity antibody fusion protein comprising or consisting of an antibody Fab or Fab' fragment with specificity for an antigen of interest, said fragment being fused to at least one single domain antibody at the C-terminus of the heavy or light chain which has specificity for a second antigen of interest.

In one embodiment the present invention provides a dual specificity antibody fusion protein comprising or consisting of an antibody Fab or Fab' fragment with specificity for an antigen of interest, said fragment being fused to two single domain antibodies wherein each single domain antibody is fused in linear sequence to each other, optionally via a linker and the resulting single domain antibody fusion is fused to the C-terminus of the light chain or the heavy chain of the Fab or Fab' fragment.

In one embodiment the present invention provides a dual specificity antibody fusion protein comprising or consisting of an antibody Fab or Fab' fragment with specificity for an antigen of interest, said fragment being fused to two single domain antibodies wherein one single domain antibody is fused to the C-terminus of the light chain of the Fab or Fab' fragment and the other single domain antibody is fused to the C-terminus of the heavy chain of the Fab or Fab' fragment, said single domain antibodies having specificity for a second antigen of interest.

In one embodiment where the heavy and light chains of the Fab or Fab' fragment each comprise a single domain antibody at the C-terminus the two single domain antibodies are identical i.e. have the same binding specificity for the same antigen. In one example, they bind the same epitope on the same antigen. For example the single domain antibodies may both be the same VH dAb, the same VHH dAb or the same VL dAb.

Preferably where the heavy and light chains of the Fab or Fab' fragment each comprise a single domain antibody at the C-terminus the two single domain antibodies are a complementary VH/VL pair which bind the antigen co-operatively i.e. they are a complementary VH/VL pair which have the same binding specificity. Typically they will be a VH/VL pair derived from the same antibody.

In one embodiment, where the dual specificity antibody fusion protein of the present invention comprises two single domain antibodies which are a complementary VH/VL pair, the VH single domain antibody is fused to the C-terminus of the heavy chain constant region (CH1) and the VL single domain antibody is fused to the C-terminus of the light chain constant region (C kappa or C lambda).

In one embodiment, where the dual specificity antibody fusion protein of the present invention comprises two single domain antibodies which are a complementary VH/VL pair, the VL single domain antibody is fused to the C-terminus of the heavy chain constant region (CH1) and the VH single domain antibody is fused to the C-terminus of the light chain constant region (C kappa or C lambda).

In dual specificity fusion proteins of the present invention the single domain antibody or antibodies bind to a second antigen, different from that bound by the Fab or Fab' fragment component.

In one example the dAbs for use in the present invention exhibit specificity for a complement pathway protein, a CD marker protein or an FcγR. In this case the dAb is preferably specific for a CD molecule. Most preferably, the dAb exhibits specificity for a CD molecule selected from the group consisting of CD68, CD80, CD86, CD64, CD3, CD4, CD8 CD45, CD16 and CD35.

In a preferred example the dAbs for use in the present invention exhibit specificity for a serum carrier protein, a circulating immunoglobulin molecule, or CD35/CR1, the serum carrier protein preferably being a human serum carrier protein such as thyroxine-binding protein, transthyretin, α1-acid glycoprotein, transferrin, fibrinogen or serum albumin. Most preferably, the dAb exhibits specificity for human serum albumin. Thus, in one example, a rabbit, mouse, rat, camel or a llama is immunised with a serum carrier protein, a circulating immunoglobulin molecule, or CD35/CR1 (e.g. human serum albumin) and blood collected when the titre is appropriate. The gene encoding the dAb may be cloned by single cell PCR, or the B cell(s) encoding the dAb may be immortalised by EBV transformation, or by fusion to an immortal cell line. Alternatively the single domain antibody may be obtained by phage display as described herein above.

In one embodiment the single domain antibody or antibodies bind human serum albumin. In one embodiment the single domain antibody or antibodies bind human serum albumin, murine serum albumin and rat serum albumin.

In one embodiment the single domain antibody which binds serum albumin is a dAb provided in WO2005/118642 (see for example FIGS. 1c and 1d) or a VHH provided in WO2004/041862 or a humanised nanobody described in, for example table III of WO2006/122787.

In one embodiment a single domain antibody which binds human serum albumin for use in the present invention is a heavy chain VH single domain antibody which comprises at least one of a CDR having the sequence given in FIG. 5 (e) SEQ ID NO:56 or FIG. 5 (k) SEQ ID NO:62 for CDR-H1, a CDR having the sequence given in FIG. 5(f) SEQ ID NO:57 or FIG. 5 (1) SEQ ID NO:63 for CDR-H2 and a CDR having the sequence given in FIG. 5 (g) SEQ ID NO:58 or FIG. 5 (m) SEQ ID NO:64 for CDR-H3.

In another embodiment a single domain antibody which binds human serum albumin for use in the present invention is a heavy chain VH antibody, wherein at least two of CDR-H1, CDR-H2 and CDR-H3 of the VH domain are selected from the following: the sequence given in SEQ ID NO:56 or SEQ ID NO:62 for CDR-H1, the sequence given in SEQ ID NO:57 or SEQ ID NO:63 for CDR-H2 and the sequence given in SEQ ID NO:58 or SEQ ID NO:64 for CDR-H3. For example, the single domain antibody may comprise a VH domain wherein CDR-H1 has the sequence given in SEQ ID NO:56 and CDR-H2 has the sequence given in SEQ ID NO:57. Alternatively, the single domain antibody may comprise a VH domain wherein CDR-H1 has the sequence given in SEQ ID NO:56 and CDR-H3 has the sequence given in SEQ ID NO:58. For the avoidance of doubt, it is understood that all permutations are included.

In another embodiment a single domain antibody which binds human serum albumin for use in the present invention is a heavy chain VH single domain antibody, wherein the VH domain comprises the sequence given in SEQ ID NO:56 for CDR-H1, the sequence given in SEQ ID NO:57 for CDR-H2 and the sequence given in SEQ ID NO:58 for CDR-H3.

In another embodiment a single domain antibody which binds human serum albumin for use in the present invention is a heavy chain VH single domain antibody, wherein the VH domain comprises the sequence given in SEQ ID NO:62 for CDR-H1, the sequence given in SEQ ID NO:63 for CDR-H2 and the sequence given in SEQ ID NO:64 for CDR-H3.

In one embodiment a single domain antibody which binds human serum albumin for use in the present invention is a humanised heavy chain VH single domain antibody, dAbH1, having the sequence given in FIG. 5 (a) (SEQ ID NO:52). An example of a suitable CH1-dAbH1 fusion comprising a G$_4$S linker is given in FIG. 6 (SEQ ID NO:68).

In one embodiment the single domain antibody which binds human serum albumin for use in the present invention is a humanised heavy chain VH single domain antibody, dAbH2, having the sequence given in FIG. 5 (c) (SEQ ID NO:54). An example of a suitable CH1-dAbH2 fusion comprising a G$_4$S linker is given in FIG. 6 (SEQ ID NO:69).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A.M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one embodiment a single domain antibody which binds human serum albumin for use in the present invention is a light chain VL single domain antibody which comprises at least one of a CDR having the sequence given in FIG. 5 (h) SEQ ID NO:59 or FIG. 5 (n) SEQ ID NO:65 for CDR-L1, a CDR having the sequence given in FIG. 5(i) SEQ ID NO:60 or FIG. 5 (o) SEQ ID NO:66 for CDR-L2 and a CDR having the sequence given in FIG. 5 (j) SEQ ID NO:61 or FIG. 5 (p) SEQ ID NO:67 for CDR-L3.

In another embodiment a single domain antibody which binds human serum albumin for use in the present invention is a light chain VL antibody, wherein at least two of CDR-L1, CDR-L2 and CDR-L3 of the VL domain are selected from the following: the sequence given in SEQ ID NO:59 or SEQ ID NO:65 for CDR-L1, the sequence given in SEQ ID NO:60 or SEQ ID NO:66 for CDR-L2 and the sequence given in SEQ ID NO:61 or SEQ ID NO:67 for CDR-L3. For example, the domain antibody may comprise a VL domain wherein CDR-L1 has the sequence given in SEQ ID NO:59 and CDR-L2 has the sequence given in SEQ ID NO:60. Alternatively, the domain antibody may comprise a VL domain wherein CDR-L1 has the sequence given in SEQ ID NO:59 and CDR-L3 has the sequence given in SEQ ID NO:61. For the avoidance of doubt, it is understood that all permutations are included.

In another embodiment a single domain antibody which binds human serum albumin for use in the present invention is a light chain VL domain antibody, wherein the VL domain comprises the sequence given in SEQ ID NO:59 for CDR-L1, the sequence given in SEQ ID NO:60 for CDR-L2 and the sequence given in SEQ ID NO:61 for CDR-L3.

In another embodiment a single domain antibody which binds human serum albumin for use in the present invention is a light chain VL domain antibody, wherein the VL domain comprises the sequence given in SEQ ID NO:65 for CDR-L1, the sequence given in SEQ ID NO:66 for CDR-L2 and the sequence given in SEQ ID NO:67 for CDR-L3.

In one embodiment a single domain antibody which binds human serum albumin for use in the present invention is a humanised light chain VL single domain antibody, dAbL1, having the sequence given in FIG. 5 (b) (SEQ ID NO:53). An example of a suitable CH1-dAbL1 fusion and a Ck1-dAbL1 fusion both comprising a G$_4$S linker is given in FIG. 6 (SEQ ID NO:70 and SEQ ID NO:72).

In one embodiment a single domain antibody which binds human serum albumin for use in the present invention is a humanised light chain VL single domain antibody, dAbL2, having the sequence given in FIG. 5 (d) (SEQ ID NO:55). An example of a suitable CH1-dAbL2 fusion and a Ck1-dAbL2 fusion both comprising a G$_4$S linker is given in FIG. 6 (SEQ ID NO:71 and SEQ ID NO:73).

In one embodiment where the heavy and light chains of the Fab or Fab' fragment each comprise a single domain antibody at the C-terminus and the two single domain antibodies are a complementary VH/VL pair which bind the antigen co-operatively as described herein above, the VH dAb is dAbH1 (SEQ ID NO:52) and the VL dAb is dAbL1 (SEQ ID NO:53).

In one embodiment where the heavy and light chains of the Fab or Fab' fragment each comprise a single domain antibody at the C-terminus the two single domain antibodies are a complementary VH/VL pair which bind the antigen co-operatively as described herein above, the VH dAb is dAbH2 (SEQ ID NO:54) and the VL dAb is dAbL2 (SEQ ID NO:55).

In another aspect, the present invention provides albumin binding antibodies or fragments thereof containing one or more of the CDRs provided herein above and in FIG. 5 (*e-p*). Said CDRs may be incorporated into any suitable antibody framework and into any suitable antibody format. Such antibodies include whole antibodies and functionally active fragments or derivatives thereof which may be, but are not limited to, monoclonal, humanised, fully human or chimeric antibodies. Accordingly, such albumin binding antibodies may comprise a complete antibody molecule having full length heavy and light chains or a fragment thereof and may be, but are not limited to Fab, modified Fab, Fab', F(ab')$_2$, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews-Online 2(3), 209-217). The methods for creating and manufacturing these antibody fragments are well known in the art (see for example Verma et al., 1998, Journal of Immunological Methods, 216, 165-181). Multi-valent antibodies may comprise multiple specificities or may be monospecific (see for example WO 92/22853 and WO05/113605). It will be appreciated that this aspect of the invention also extends to variants of these albumin binding antibodies.

It will be appreciated that such albumin binding antibodies, in particular single domain antibodies may be conjugated to any other antibody or protein or other molecule, as desired or used in any other suitable context. In one example the single domain antibodies dAbH1, dAbL1, dAbH2, dAbL2 as described above and shown in FIG. 5 (*a-d*) may be incorporated into any suitable antibody format or used as single domain antibodies in any suitable context, such as a fusion or conjugate.

In one embodiment antibodies of this aspect of the invention comprise the sequence given in FIG. 5(*e*) for CDR-H1, the sequence given in FIG. 5(*f*) for CDR-H2 and the sequence given in FIG. 5(*g*) for CDR-H3.

In one embodiment antibodies of this aspect of the invention comprise the sequence given in FIG. 5(*k*) for CDR-H1, the sequence given in FIG. 5(*l*) for CDR-H2 and the sequence given in FIG. 5(*m*) for CDR-H3.

In one embodiment antibodies of this aspect of the invention comprise the sequence given in FIG. 5(*h*) for CDR-L1, the sequence given in FIG. 5(*i*) for CDR-L2 and the sequence given in FIG. 5(*j*) for CDR-L3.

In one embodiment antibodies of this aspect of the invention comprise the sequence given in FIG. 5(*n*) for CDR-L1, the sequence given in FIG. 5(*o*) for CDR-L2 and the sequence given in FIG. 5(*p*) for CDR-L3.

Where the single domain antibody or antibodies of the dual specificity fusion protein of the present invention bind to albumin the binding affinity of the single domain antibody for albumin will be sufficient to extend the half-life of the Fab or Fab' in vivo. It has been reported that an affinity for albumin of less than or equal to 2.5 µM affinity will extend half-life in vivo (Nguyen, A. et al (2006) Protein Engineering, Design & Selection, 19(7), 291-297). The single domain antibody molecules of the present invention preferably have a binding affinity suited to their purpose and the antigen to which they bind. In one example the single domain antibodies have a high binding affinity, for example picomolar. In one example the single domain antibodies have a binding affinity for antigen which is nanomolar or micromolar.

Affinity may be measured using any suitable method known in the art, including BIAcore as described in the Examples herein using natural or recombinant antigen.

Preferably the single domain antibody molecules of the present invention which bind albumin have a binding affinity of about 2 µM or better. In one embodiment the single domain antibody molecule of the present invention has a binding affinity of about 1 µM or better. In one embodiment the single domain antibody molecule of the present invention has a binding affinity of about 500 nM or better. In one embodiment the single domain antibody molecule of the present invention has a binding affinity of about 200 nM or better. In one embodiment the domain antibody molecule of the present invention has a binding affinity of about 1 nM or better. It will be appreciated that the affinity of single domain antibodies provided by the present invention and known in the art may be altered using any suitable method known in the art. The present invention therefore also relates to variants of the domain antibody molecules of the present invention, which have an improved affinity for albumin. Such variants can be obtained by a number of affinity maturation protocols including mutating the CDRs (Yang et al., J. Mol. Biol., 254 392-403, 1995), chain shuffling (Marks et al., Bio/Technology, 10 779-783, 1992), use of mutator strains of *E. coli* (Low et al., J. Mol. Biol., 250 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The present invention also provides an isolated DNA sequence encoding a dual specificity antibody fusion protein of the present invention. The DNA sequences of the present invention may comprise synthetic DNA, for instance produced by chemical processing, cDNA, genomic DNA or any combination thereof.

DNA sequences which encode the dual specificity antibody fusion protein of the present invention can be obtained by methods well known to those skilled in the art. For example, DNA sequences coding for part or all of the antibody fragments, linkers and/or dAbs may be synthesised as desired from the determined DNA sequences or on the basis of the corresponding amino acid sequences.

Standard techniques of molecular biology may be used to prepare DNA sequences coding for the dual specificity antibody fusion protein of the present invention. Desired DNA sequences may be synthesised completely or in part using oligonucleotide synthesis techniques. Site-directed mutagenesis and polymerase chain reaction (PCR) techniques may be used as appropriate.

The present invention further relates to a cloning or expression vector comprising one or more DNA sequences of the present invention. Accordingly, provided is a cloning or expression vector comprising one or more DNA sequences encoding a dual specificity antibody fusion protein of the present invention. In one preferred embodiment, the cloning or expression vector comprises a single DNA sequence encoding the entire dual specificity antibody fusion protein. Thus, the cloning or expression vector comprises DNA encoded transcription units in sequence such that a translation fusion protein is produced.

Indeed, it will be understood by those skilled in the art that a fusion protein of the invention can have the dAb at the N-terminus or the C-terminus and thus, the dAb DNA encoded transcription unit will be first or last, respectively, within the DNA sequence encoding the translation fusion. Thus, a translation fusion may comprise an N-terminal dAb and a C-terminal Fab or Fab'. Further, a translation fusion may comprise an N-terminal Fab or Fab' and a C-terminal dAb.

It will be appreciated that the heavy chain and light chain of the Fab or Fab' may be incorporated into the same or different vectors. In one embodiment one vector may comprise a translation fusion comprising a Fab or Fab' heavy chain and a C-terminal dAb and another vector may comprise a translation fusion comprising a Fab or Fab' light chain and a C-terminal dAb.

For example, where the desire is to produce a dual specificity antibody fusion protein with the dAb moiety at the N-terminal end of the antibody fragment, the vector will comprise DNA transcription units in sequence order; a DNA transcription unit encoding the dAb moiety, optionally a DNA transcription unit encoding a linker sequence, and a DNA transcription unit encoding an antibody fragment. Where the desire is to produce a dual specificity antibody fusion protein with the dAb moiety at the C-terminal end of the antibody fragment, the vector will comprise DNA transcription units in sequence order; a DNA transcription unit encoding an antibody fragment, optionally a DNA transcription unit encoding a linker sequence, and a DNA transcription unit encoding dAb moiety with specificity for a serum carrier protein, a circulating immunoglobulin molecule, or CD35/CR1, for example, human serum albumin. Thus, a translation fusion of the invention can be in different configurations including, for example but without limitation, dAb-linker-Fab, Fab-linker-dAb, dAb-Fab, Fab-dAb, Fab'-dAb, dAb-Fab', dAb-linker Fab', Fab'-linker-dAb. Where two vectors are used for example, the first may comprise the heavy chain of a Fab or Fab' fused to a dAb and the second may comprise the light chain of a Fab or Fab' fused to a dAb.

DNA code for an antibody fragment comprised within a translation fusion of the invention can be incorporated into a vector as a transcription unit in configurations as known to the person skilled in the art, for example a transcription unit can comprise code for the light chain followed by the heavy chain code, or vice versa; see, in particular, Humphreys et al., 2002, Protein Expression and Purification, 26:309-320.

Preferably, a vector according to the present invention comprises an appropriate leader sequence, such as an antibody leader sequence. Such leader sequences are well known in the art.

General methods by which the vectors may be constructed, transfection and transformation methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding a dual specificity antibody fusion protein of the present invention. Any suitable host cell/vector system may be used for expression of the DNA sequences encoding the dual specificity antibody fusion protein. Bacterial, for example *E. coli*, and other microbial systems may be used or eukaryotic, for example mammalian, host cell expression systems may also be used. Suitable mammalian host cells include NS0, CHO, myeloma or hybridoma cells. Accordingly in one embodiment the fusion protein of the present invention is expressed in *E. coli*. In another embodiment the fusion protein of the present invention is expressed in mammalian cells.

The present invention also provides a process for the production of a dual specificity antibody fusion protein comprising culturing a host cell comprising a vector of the present invention under conditions suitable for the expression of protein from the DNA sequence encoding said dual specificity antibody fusion protein. The invention further provides methods for isolating the dual specificity antibody fusion protein.

On production, a dual specificity antibody fusion protein of the present invention may be purified, where necessary, using any suitable method known in the art. For example, but without limitation, chromatographic techniques such as ion exchange, size exclusion, protein G or hydrophobic interaction chromatography may be used.

The size of a dual specificity antibody fusion protein may be confirmed by conventional methods known in the art such as size exclusion chromatography and non-reducing SDS-PAGE. Such techniques can be used to confirm that the protein has not dimerised and/or does not have a portion missing, e.g. the dAb portion. If dimers are detected then the monomeric dual specificity antibody fusion protein may be purified away from the dimeric species using conventional chromatography techniques as described above.

Dual specificity antibody fusion proteins of the invention are useful in the treatment of diseases or disorders including inflammatory diseases and disorders, immune disease and disorders, fibrotic disorders and cancers.

The term "inflammatory disease" or "disorder" and "immune disease or disorder" includes rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease.

The term "fibrotic disorder" includes idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery.

The term "cancer" includes a malignant new growth that arises from epithelium, found in skin or, more commonly, the lining of body organs, for example: breast, ovary, prostate, lung, kidney, pancreas, stomach, bladder or bowel. Cancers tend to infiltrate into adjacent tissue and spread (metastasise) to distant organs, for example: to bone, liver, lung or the brain.

Thus, according to a further aspect of the invention, there is provided a pharmaceutical composition which comprises an antibody fusion of the invention in association with one or more pharmaceutically acceptable carriers, excipients or diluents. Also provided is the use of an antibody fusion protein of the invention for the manufacture of a medicament for the treatment of a disease or disorder. Most preferably, the disease or disorder is an inflammatory disease or disorder.

Pharmaceutical compositions according to the invention may take a form suitable for oral, buccal, parenteral, subcutaneous, nasal, topical, ophthalmic or rectal administration, or a form suitable for administration by inhalation or insufflation.

Where appropriate, for example if the single domain antibody or antibodies of the antibody fusion protein bind to albumin, it may be desirable to pre-formulate the dual specificity fusion protein with human or recombinant serum albumin, using any suitable method known in the art.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The bispecific antibodies of the invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the bispecific antibodies of the invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

The invention will now be described with reference to the following examples, which are merely illustrative and should not in any way be construed as limiting the scope of the present invention.

LIST OF FIGURES

Figure 2:
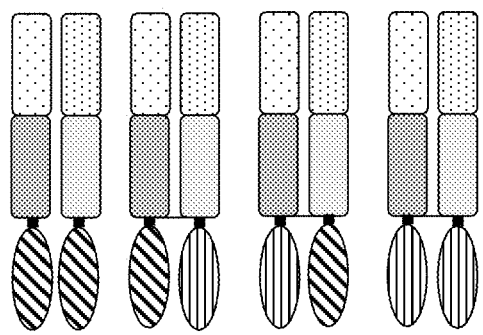

FIG. 1: Diagrammatic representation of Fab-dAbs where the dAb is at the C-terminus FIG. 2: Diagrammatic representation of Fab-didAbs FIG. 3. SDS PAGE analysis of FabA-dAbL3 (CK-SG$_4$SE) (1) and FabA-dAbL3 (CK-G[APAPA]$_2$) (2).

Figure 4:
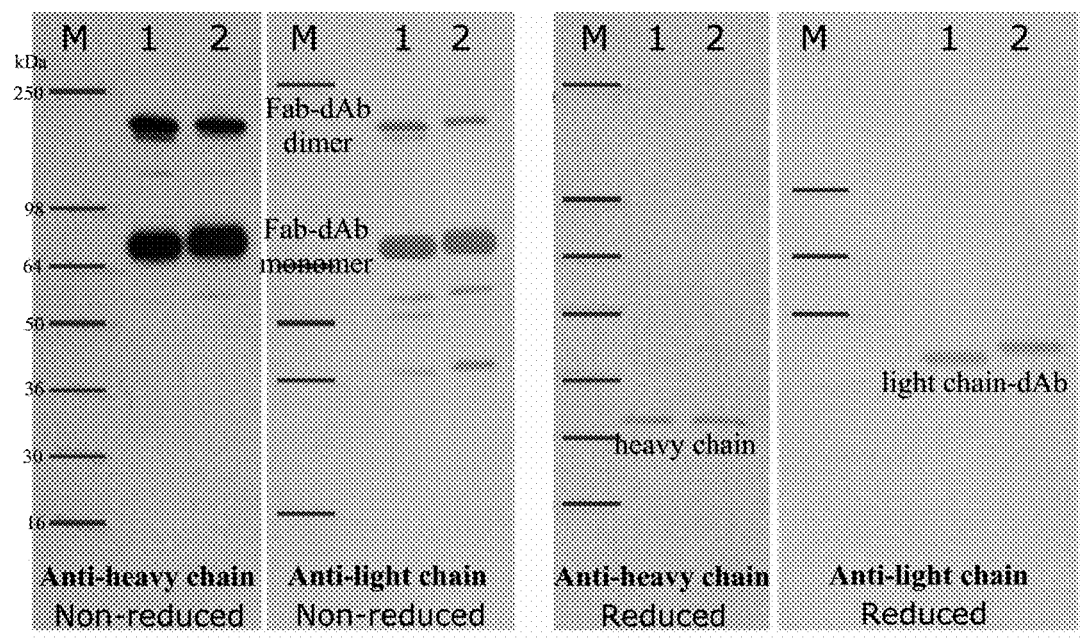

FIG. 4: Western blot analysis of FabA-dAbL3 (CK-SG$_4$SE) (1) and FabA-dAbL3 (CK-G[APAPA]$_2$) (2).

Figure 4A:
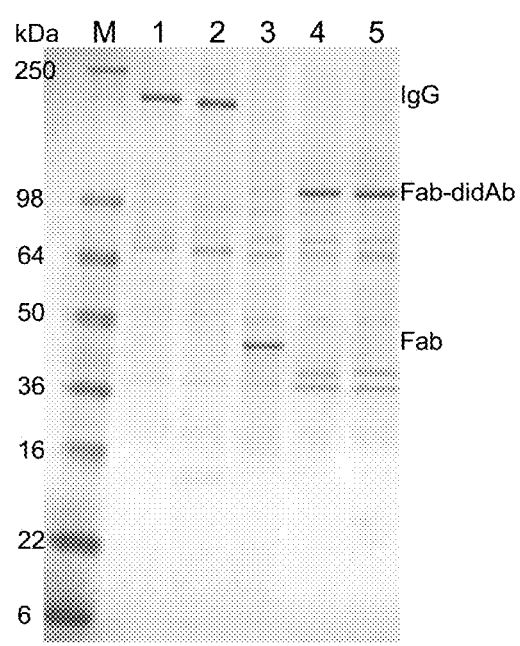

FIG. 4a: SDS PAGE of FabB-didAbs
Lane M=SeeBlue markers
Lanes 1 & 2=IgG control
Lane 3=FabB
Lane 4=FabB-didAb, -dAbL1 (CK-G4Sx2) & dAbH1 (CH1-G4Sx2)
Lane 5=FabB-didAb, -dAbL2 (CK-G4Sx2) & dAbH2 (CH1-G4Sx2)

FIG. 5: Sequences of domain antibodies dAbH1 (a), dAbH2 (b), dAbL1 (c) and dAbL2 (d) and the CDRs derived from each of those antibodies.

```
CDRs for dAbH1
                                        (SEQ ID NO: 56)
    e) CDRH1: GIDLSNYAIN;

(SEQ ID NO: 57)
    f) CDRH2: IIWASGTTFYATWAKG;
```

-continued g) CDRH3: TVPGYSTAPYFDL;                    (SEQ ID NO: 58)

CDRs for dAbH2 h) CDRL1: QSSPSVWSNFLS;                     (SEQ ID NO: 59)

I) CDRL2: EASKLTS;                          (SEQ ID NO: 60)

j) CDRL3: GGGYSSISDTT;                      (SEQ ID NO: 61)

CDRs for dAbL1 k) CDRH1: GFSLSRYAMT;                       (SEQ ID NO: 62)

l) CDRH2: TITTGGNTNYANWAKG;                 (SEQ ID NO: 63)

m) CDRH3: GGYVSYADATELSL;                   (SEQ ID NO: 64)
and

CDRs for dAbL2 n) CDRL1: AQSQSIGSRLA;                      (SEQ ID NO: 65)

o) CDRL2: YASTVAS;                          (SEQ ID NO: 66)

p) CDRL#: QSYDYSSSSSYA.                     (SEQ ID NO: 67)

FIG. 6: FabB-dAb constructs comprising FabB heavy or light chain variable domain fused to a domain antibody. A—FabB-dabH1 (CH1-G$_4$Sx2); B—FabB-dabH2 (CH1-G$_4$Sx2); C—FabB-dabL1 (CH1-G$_4$Sx2); D—FabB-dabL2 (CH1-G$_4$Sx2); E—FabB-dabL1 (CK-G$_4$Sx2); F—FabB-dabL2 (CK-G$_4$Sx2).

FIG. 7: Fab'A heavy and light chain sequences and FabA heavy chain sequence.

EXPERIMENTAL

Example 1

Production of a dAb Specific for Human Serum Albumin

An in-frame DNA encoded transcription unit encoding a dAb with specificity for human serum albumin was produced using recombinant DNA technology.

Where desired an in-frame DNA encoded transcription unit encoding a dAb with specificity for a recruitment protein can be produced using recombinant DNA technology.

Example 2

Production of Antibody Fragment

For fusion of a dAb to the C-terminus of the light chain, DNA was synthesised encoding a human kappa light chain constant region (with the Km3 allotype of the kappa constant region), a peptide linker and a dAb and cloned as a SacI-PvuII restriction fragment into the UCB-Celltech in-house expression vector pTTOD(Fab) (a derivative of pTTO-1, described in Popplewell et al., Methods Mol. Biol. 2005; 308: 17-30) which contains DNA encoding the human gamma-1 CH1 constant region. This gave rise to a dicistronic gene arrangement consisting of the gene for the humanised light chain fused via a linker to a dAb followed by the gene for the humanised heavy chain Fab fragment, both under the control of the tac promoter. Also encoded is a unique BspE1 site upstream of the Gly4Ser linker, or an AscI site upstream of the Ala-Pro-rich linker.

For fusion of a dAb the C-terminus of the heavy chain, DNA was synthesised encoding a human CH1 fragment (of the γ1 isotype) followed by a linker encoding sequence and a dAb. This was sublcloned as an ApaI-EcoRI restriction fragment into the UCB-Celltech in-house expression vector pTTOD(Fab) (a derivative of pTTO-1, described in Popplewell et al., above) which contains DNA encoding the human gamma-1 CH1 constant region. This gave rise to a dicistronic gene arrangement consisting of the gene for the humanised light chain a non-coding intergenic sequence and followed by a heavy chain fused via a linker to a dAb, both under the control of the tac promoter. The recombinant expression plasmid was transformed into the E. coli strain W3110 in which expression is induced by addition of IPTG. Expression experiments were performed at small scale initially (5 ml culture volumes) with addition of 200 uM IPTG at OD (600 nm) of approx. 0.5, cells were harvested 2 hours post induction and extracted overnight at 30° C. in Tris/EDTA. Clarified extracts were used for affinity analysis by Biacore. Constructs giving promising expression yields and activities were selected for fermentation.

Methods

In the following examples the antibody chain to which the dAb is fused is denoted either as CK or LC for the cKappa light chain and as CH1 or HC for the heavy chain constant domain, CH1.

Construction of FabA-dAb Fusion Plasmids for Expression in E. coli

Fab-dAb fusion proteins were constructed by fusing dAbL3 or dAbH4 to the C-terminus of the constant region of either the light or heavy chain of FabA. A flexible (SGGGGSE (SEQ ID NO:1)) or a rigid (G(APAPA)$_2$ (SEQ ID NO: 34)) linker was used to link the dAb to the cKappa region (SEQ ID NO:75) whereas the linker DKTHTS (SEQ ID NO:2) was used to link the dAb to the CH1 region (SEQ ID NO:76). The DNA sequence coding for the constant region-dAb fusion was manufactured synthetically as fragments to enable sub-cloning into the FabA sequence of the in-house pTTOD vector.

Light chain-dAb fusions were constructed by sub-cloning the SacI-ApaI fragment of the synthesized genes, encoding a C-terminal cKappa fused to either dAbL3 or dAbH4 via either a (SGGGGSE (SEQ ID NO:1)) or a rigid (G(APAPA)$_2$ (SEQ ID NO: 34)) linker, into the corresponding sites of a plasmid capable of expressing FabA. Heavy chain-dAb fusions were constructed by sub-cloning the ApaI-EcoRI fragment of the synthesised genes, encoding a C-terminal CH1 fused to either dAbL3 or dAbH4 via a DKTHTS linker, into the corresponding sites of a plasmid capable of expressing FabA.

Fab' A is derived from an IL-1 beta binding antibody, the heavy and light chain sequences of which are provided in SEQ ID NOs:74 and 75 respectively as shown in FIG. 7. In Fab'A where the light chain has a dAb attached, the hinge of the heavy chain was altered to DKTHTS even where no dAb is attached to the heavy chain (SEQ ID NO:76).

FabA comprises the same light chain sequence (SEQ ID NO:75) and a truncated heavy chain sequence which terminates at the interchain cysteine (SEQ ID NO:77). dAbL3 and dAbH4 are light and heavy chain domain antibodies respectively which bind human serum albumin.

Construction of FabA-didAb fusion plasmids for expression in *E. coli* FabA-didAb with dAbL3 or dAbH4 on both light and heavy chains were constructed by sub-cloning the ApaI-EcoRI fragment coding for CH1-dAb fusions into the existing Fab-dAb plasmids where the dAb is fused to the light chain via the flexible linker.

Construction of FabB-dAb Fusion Plasmids for Expression in Mammalian Cells

The FabB-dAbs, FabB-dAbH1 (CH1-$G_4$Sx2), FabB-dAbH2 (CH1-$G_4$Sx2), FabB-dAbL1 (CH1-$G_4$Sx2), FabB-dAbL2 (CH1-$G_4$Sx2) were all assembled by PCR then cloned into a mammalian expression vector under the control of the HCMV-MIE promoter and SV40E polyA sequence. These were paired with a similar vector containing the FabB light chain for expression in mammalian cells (see below).

FabB is derived from an antibody which bids a cell surface co-stimulatory molecule. dAbH1, dAbH2, dAbL1 and dAbL2 were obtained as described in Example 3.

Construction of FabB-dAb Fusion Plasmids for Expression in Mammalian Cells

The FabB-dAbs, FabB-dAbH1 (CH1-$G_4$Sx2), FabB-dAbH2 (CH1-$G_4$Sx2), FabB-dAbL1 (CK-$G_4$Sx2), FabB-dAbL2 (CK-$G_4$Sx2) were all assembled by PCR then cloned into a mammalian expression vector under the control of the HCMV-MIE promoter and SV40E polyA sequence.

Mammalian Expression of FabB-dAbs and didAbs

HEK293 cells were transfected with the heavy and light chain plasmids using Invitrogen's 293fectin transfection reagent according to the manufacturer's instructions. Briefly, 2 µg heavy chain plasmid+2 µg light chain plasmid was incubated with 10 µl 293 fectin+340 µl Optimem media for 20 mins at RT. The mixture was then added to 5×10$^6$ HEK293 cells in suspension and incubated for 4 days with shaking at 37° C.

Biacore

Binding affinities and kinetic parameters for the interactions of Fab-dAb constructs were determined by surface plasmon resonance (SPR) conducted on a Biacore T100 using CM5 sensor chips and HBS-EP (10 mM HEPES (pH7.4), 150 mM NaCl, 3 mM EDTA, 0.05% v/v surfactant P20) running buffer. Fab-dAb samples were captured to the sensor chip surface using either a human F(ab')$_2$-specific goat Fab (Jackson ImmunoResearch, 109-006-097) or an in-house generated anti human CH1 monoclonal antibody. Covalent immobilisation of the capture antibody was achieved by standard amine coupling chemistry.

Each assay cycle consisted of firstly capturing the Fab-dAb using a 1 min injection, before an association phase consisting of a 3 min injection of antigen, after which dissociation was monitored for 5 min. After each cycle, the capture surface was regenerated with 2×1 min injections of 40 mM HCl followed by 30 s of 5 mM NaOH. The flow rates used were 10 µl/min for capture, 30 µl/min for association and dissociation phases, and 10 µl/min for regeneration.

For kinetic assays, a titration of antigen (for human serum albumin typically 62.5 nM-2 µM, for IL-1β 1.25-40 nM) was performed, a blank flow-cell was used for reference subtraction and buffer-blank injections were included to subtract instrument noise and drift.

Kinetic parameters were determined by simultaneous global-fitting of the resulting sensorgrams to a standard 1:1 binding model using Biacore T100 Evaluation software.

In order to test for simultaneous binding, 3 min injections of either separate 5 µM HSA or 100 nM IL-1β, or a mixed solution of 5 µM HSA and 100 nM IL-1β were injected over the captured Fab-dAb.

Fab-dAb Purification from *E. coli*

Periplasmic Extraction

*E. coli* pellets containing the Fab-dAbs within the periplasm were re-suspended in original culture volume with 100 mM Tris/HCl, 10 mM EDTA pH 7.4. These suspensions were then incubated at 4° C. for 16 hours at 250 rpm. The re-suspended pellets were centrifuged at 10000×g for 1 hour at 4° C. The supernatants were removed and 0.45 µm filtered.

Protein-G Capture

The Fab-dAbs were captured from the filtered supernatant by Protein-G chromatography. Briefly the supernatants were applied, with a 20 minute residence time, to a Gammabind Plus Sepharose (GE Healthcare) column equilibrated in 20 mM phosphate, 150 mM NaCl pH7.1. The column was washed with 20 mM phosphate, 150 mM NaCl pH7.1 and the bound material eluted with 0.1M glycine/HCl pH2.8. The elution peak was collected and pH adjusted to ~pH5 with 1M sodium acetate. The pH adjusted elutions were concentrated and diafiltered into 50 mM sodium acetate pH4.5 using a 10 k MWCO membrane.

Ion Exchange

The Fab-dAbs were further purified by cation exchange chromatography at pH4.5 with a NaCl elution gradient. Briefly the diafiltered Protein-G eluates were applied to a Source15S (GE Healthcare) column equilibrated in 50 mM sodium acetate pH4.5. The column was washed with 50 mM sodium acetate pH4.5 and the bound material eluted with a 20 column volume linear gradient from 0 to 1M NaCl in 50 mM sodium acetate pH4.5. Third column volume fractions were collected through out the gradient. The fractions were analysed by A280 and SDS-PAGE and relevant fractions pooled.

Gel Filtration

If required the Fab-dAbs were further purified by gel filtration. Briefly the FabA-dAbL3 (CK-SG$_4$SE) pooled ion exchange elution fractions were applied to a Superdex200 (GE Healthcare) column equilibrated in 50 mM sodium acetate, 125 mM NaCl pH 5.0 and eluted with an isocratic gradient of 50 mM sodium acetate, 125 mM NaCl pH 5.0. 1/120 column volume fractions were collected through out the gradient. The fractions were analysed by A280 and SDS-PAGE and relevant fractions pooled.

For the Fab-dAbs that did not undergo gel filtration, the pooled ion exchange elution fractions were concentrated and diafiltered into 50 mM sodium acetate, 125 mM NaCl pH 5.0 using a 10 k MWCO membrane.

SDS-PAGE

Samples were diluted with water where required and then to 10 µl was added 10 µL 2× sample running buffer. For non-reduced samples, 2 µL of 100 mM NEM was added at this point, for reduced samples 2 µL of 10× reducing agent was added. The sample were vortexed, incubated at 85° C. for 5 mins, cooled and centrifuged at 12500 rpm for 30 secs. The prepared samples were loaded on to a 4-20% acrylamine Tris/Glycine SDS gel and run for 100 mins at 125V. The gels were either transferred onto PVDF membranes for Western blotting or stained with Coomassie Blue protein stain.

Western Blotting

Gels were transferred to PVDF membranes in 12 mM Tris, 96 mM glycine pH8.3 for 16 hours at 150 mA. The PVDF membrane was block for 1 hr with 2% Marvel™ in PBS+0.1% Tween20 (Blocking buffer)

Anti-Light Chain

HRP-rabbit anti-human kappa light chains, 1/5000 dilution in blocking buffer for 1 hr.

Anti-Heavy Chain mouse anti-human heavy chain, 1/7000 dilution in blocking buffer for 1 hr. Followed by HRP-goat anti-mouse, 1/2000 dilution in blocking buffer for 1 hr.

Anti-his Tag rabbit anti-His6, 1/1000 dilution in blocking buffer for 1 hr. Followed by HRP-goat anti-rabbit IgG, 1/1000 dilution in blocking buffer for 1 hr.

All blots were washed 6 times with 100 ml PBS+0.1% Tween20 for 10 minutes per wash. The blots were developed with either ECL reagent for 1 min before being exposed to Amersham Hyperfilm, or metal enhanced DAB reagent for 20-30 minutes followed by water.

High Temperature Reverse Phase HPLC

Samples (2 µg) were analysed on a 2.1 mm C8 Poroshell column at 80° C., with a flow rate of 2 ml/min and a gradient of 18-38% B over 4 mins.

A=0.1% TFA in $H_2O$
B=0.065% TFA in 80:20 IPA:MeOH
Detection is by absorption at 214 nm.

ELISA

The yields of Fab-dAb were measured using a sandwich ELISA. Briefly, the Fab-dAb was captured with an anti-CH1 antibody then revealed with an anti-kappa-HRP.

Example 3

Generating Anti-Albumin Antibodies

½ lop rabbits were immunised with recombinant chromapure human serum albumin (purchased from Jackson). Rabbits received 3 immunisations of 100 ug HSA protein sub cutaneously, the first immunisation in complete Freunds adjuvant and subsequent immunisations in incomplete Freunds. Antibodies 1 and 2 which bind human, mouse and rat serum albumin were isolated using the methods described in WO04/051268. Genes for the heavy chain variable domain (VH) and light chain variable domain (VL) of antibodies 1 and 2 were isolated and sequenced following cloning via reverse transcription PCR.

The light chain grafted sequences were sub-cloned into the rabbit light chain expression vector pVRbcK which contains the DNA encoding the rabbit C-Kappa constant region. The heavy chain grafted sequences were sub-cloned into the rabbit heavy chain expression vector pVRbHFab, which contains the DNA encoding the rabbit Fab' heavy chain constant region. Plasmids were co-transfected into CHO cells and the antibodies produced screened for albumin binding and affinity (Table 1). Transfections of CHO cells were performed using the Lipofectamine™ 2000 procedure according to manufacturer's instructions (InVitrogen, catalogue No. 11668).

Generating Humanised Domain Antibodies dAbL1, dAbH1, dAbL2 and dAbH2

Humanised VL and VH regions were designed using human V-region acceptor frameworks and donor residues in the framework regions. One grafted VL region (L1 (SEQ ID NO:53) and L2 (SEQ ID NO:55)) and one VH region (H1 (SEQ ID NO:52) and H2 (SEQ ID NO:54)) were designed for each of antibodies 1 and 2 and genes were built by oligonucleotide assembly and PCR mutagenesis. The grafted domain antibodies and their CDRs are shown in FIG. 5.

TABLE 1

Affinities of anti-albumin antibodies

| | as rabbit Fab | | as humanised IgG |
|---|---|---|---|
| | Human SA nM | murineSA nM | Human SA nM |
| Antibody 1 | 0.31 | 2.6 | 0.82 |
| Antibody 2 | 0.33 | 12 | 0.13 |

Example 4

Analysis of FabB-dAbs Expressed in Mammalian Cells

FabB-dAb constructs were produced as described in the methods and the supernatants from the tranfected HEK293 cells containing the FabB-dAbs were tested directly in BIAcore.

Kinetic analysis was conducted to assess the interaction of HSA with FabB-dAb constructs. These consisted of either dAbL1, dAbH2 or dAbL3 fused to the C-terminus of CH1 of FabB (See FIG. 6). The FabB-dAbL1 has a higher affinity for HSA, $K_D$=170 nM, than FabB-dAbL3, $K_D$=392 nM. The FabB-dAbH2 was shown to possess the poorest affinity towards HSA, $K_D$=1074 nM, see Table 2.

TABLE 2

| Construct | $k_a$ (×$10^4 M^{-1}s^{-1}$) | $k_d$ (×$10^{-3}s^{-1}$) | $K_D$ (×$10^{-9}M$) |
|---|---|---|---|
| FabB-dAbL1 (CH1-$G_4Sx2$) | 1.91 ± 0.74 | 2.18 ± 1.21 | 170 ± 78 |
| FabB-dAbH2 (CH1-$G_4Sx2$) | 2.66 ± 0.39 | 29 ± 4.76 | 1074 ± 42 |
| FabB-dAbL3 (CH1-$G_4Sx2$) | 2.63 ± 0.39 | 9.87 ± 1.63 | 392 ± 119 |

Affinity and kinetic parameters determined for the binding of HSA to FabBs fused to dAbL1, dAbH2 or dAbL3.
The data shown are mean values ± SEM. (For FabB-dAbL1 and FabB-dAbH2 n = 4. For FabB-dAbL3 n = 2).

SDS-PAGE and western blotting of the FabB-dAb proteins confirmed that the FabB-dAbs produced were of the expected size.

Example 5

Analysis of FabB-didAbs Expressed in Mammalian Cells

FabB-didAb constructs were produced as described in the methods and the supernatants from the tranfected HEK293 cells containing the didAbs tested directly in BIAcore.

Further analysis was performed using didAb constructs in which single dAbs were fused to both heavy and light C-termini of Fab. Constructs in which the didAb was derived from a natural heavy and light variable domain pairing showed a marked improvement in affinity compared to the single dAb alone (table 2 and 3). The didAb fusion consisting of two identical dAbL1s showed no improvement in affinity over that seen for the single dAbL1 (data not shown).

TABLE 3

| Construct | $k_a$ (×$10^4 M^{-1}s^{-1}$) | $k_d$ (×$10^{-3}s^{-1}$) | $K_D$ (×$10^{-9}M$) |
|---|---|---|---|
| FabB-didAb, -dAbL1 (CK-$G_4Sx2$) & dAbH1 (CH1-$G_4Sx2$) | 1 | 0.16 | 9 |

TABLE 3-continued

| Construct | $k_a$ (×10$^4$M$^{-1}$s$^{-1}$) | $k_d$ (×10$^{-3}$s$^{-1}$) | $K_D$ (×10$^{-9}$M) |
|---|---|---|---|
| FabB-didAb, -dAbL2 (CK-G$_4$Sx2) & dAbH2 (CH1-G$_4$Sx2) | 0.54 | 0.21 | 39 |

Affinity and kinetic parameters determined for the binding of HSA to FabBs fused to both dAbL1 & dAbH1 or dAbL2 & dAbH2.

SDS-PAGE of the FabB-didAb proteins confirmed that the FabB-didAbs expressed well and were of the expected size (See FIG. 4a). Note this SDS PAGE gel is total protein expressed by the cell.

Example 6

Analysis of Purified FabA-dAbs

Plasmids for expression of the Fab-dAbs, Fab'A-dAbL3 (CK-SG$_4$SE) Fab'A-dAbL3 (CK-G[APAPA]$_2$) in *E. coli* were constructed as described in the methods. The Fab-dAbs were expressed into the periplasm of the *E. coli* and purified to homogeneity as described in the methods. The purity of the Fab-dAbs were assessed by high temperature reverse phase HPLC, SDS-PAGE and Western blotting. The Fab-dAbs were also assessed for antigen binding by Biacore.

High Temperature Reverse Phase HPLC

High temperature reverse phase HPLC as performed as described in the methods gave quantitative analysis of all species contained in FabA-dAbL3 (CK-SG$_4$SE) and FabA-dAbL3 (CK-G[APAPA]$_2$). The percentage of each species present is shown in table 4.

TABLE 4

Quantification of species present in Fab-dAb batches

| Species | Fab'A-dAbL3 (CK-SG$_4$SE) | Fab'A-dAbL3 (CK-G[APAPA]$_2$) |
|---|---|---|
| 1 | 0.6% | 1.8% |
| 2 | 0.6% | 0.0% |
| 3 | 1.0% | 0.3% |
| 4 | 0.9% | 0.8% |
| Fab-dAb | 85.5% | 92.9% |
| Di Fab-dAb | 11.5% | 4.2% |

SDS-PAGE

Figure 3:
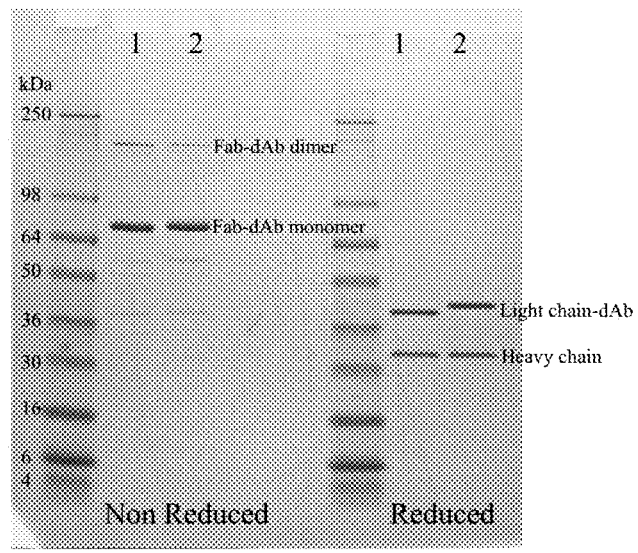

Fab-dAb samples were prepared under non-reduced and reduced conditions and run on a gel as described in the methods. The gel was Coomassie stained. The banding profile of both Fab-dAb samples, Fab'A-dAbL3 (CK-SG$_4$SE) and Fab'A-dAbL3 (CK-G[APAPA]$_2$), corresponds well to the profile observed by high temperature reverse phase HPLC (FIG. 3).

Western Blot

Fab-dAb samples were subjected to non-reduced SDS-PAGE followed by western blot analysis with anti-light chain and anti-heavy chain antibodies as described in the methods. This confirmed that the dAb was on the light chain of the Fab and that the heavy chain was unmodified in both samples (FIG. 4). It also demonstrates that all bands detected by coomassie stained, non-reduced SDS PAGE are Fab-dAb related products.

Biacore

Kinetic analysis by SPR as described in the methods was used to assess the binding of human serum albumin to Fab'A-dAbL3 (CK-SG$_4$SE) and Fab'A-dAbL3 (CK-G[APAPA]$_2$). The results in table 5 demonstrate that both constructs are able to bind human serum albumin with a similar affinity ($K_D$) of approximately 1 µM.

TABLE 5

| Construct | $k_a$ (×10$^4$M$^{-1}$s$^{-1}$) | $k_d$ (×10$^{-2}$s$^{-1}$) | $K_D$ (×10$^{-9}$M) |
|---|---|---|---|
| Fab'A-dAbL3 (CK-SG$_4$SE) | 3.44 | 1.42 | 411 |
| Fab'A-dAbL3 (CK-G[APAPA]$_2$) | 9.61 | 2.85 | 296 |

Further kinetic analysis demonstrated that all the fusion constructs retained the interaction characteristics of the original FabA towards IL-1β, table 6, with only minor differences seen in the kinetic and affinity parameters.

TABLE 6

| Construct | $k_a$ (×10$^5$M$^{-1}$s$^{-1}$) | $k_d$ (×10$^{-5}$s$^{-1}$) | $K_D$ (×10$^{-12}$M) |
|---|---|---|---|
| Fab'A-dAbL3 (CK-SG$_4$SE) | 1.90 | 4.21 | 221 |
| Fab'A-dAbL3 (CK-G[APAPA]$_2$) | 2.17 | 3.99 | 184 |
| Fab'A | 2.02 | 6.46 | 320 |

The potential for each construct to bind simultaneously to both human serum albumin and the IL-1β antigen was assessed by capturing each construct to the sensor chip surface, before performing either separate 3 min injections of 5 µM human serum albumin or 100 nM IL-1β, or a mixed solution of both 5 µM human serum albumin and 100 nM IL-1β. For each Fab-dAb construct the response seen for the combined HSA/IL-1β solution was almost identical to the sum of the responses of the independent injections, see table 7. This shows that the Fab-dAbs are capable of simultaneous binding to both IL-1β and human serum albumin, and that binding of either IL-1β or human serum albumin does not inhibit the interaction of the other. The original FabA bound only to IL-1β, with negligible binding to human serum albumin.

TABLE 7

| Construct | Analyte | Binding | (RU) |
|---|---|---|---|
| Fab'A-dAbL3 (CK-SG$_4$SE) | HSA + IL-1β | 37.6 | (37.9) |
| | HSA | 13.2 | |
| | IL-1β | 24.7 | |
| Fab'A-dAbL3 (CK-G[APAPA]$_2$) | HSA + IL-1β | 61.9 | (63.6) |
| | HSA | 30.7 | |
| | IL-1β | 32.9 | |
| Fab'A | HSA + IL-1β | 30.3 | (30.0) |
| | HSA | 1.3 | |
| | IL-1β | 28.7 | |

The table above shows the binding response (RU) seen for each construct after separate injections of HSA or IL-1β, or injection of premixed HSA and IL-1β. In each case the final concentration was 5 µM for HSA and 100 nM for IL-1β. The sum of the individual HSA and IL-1β responses is shown in parentheses.

Example:7

FabA didAbs

Expression of FabA-didAbs in *E. coli*

FabA-dAbs and FabA-didAb fusions terminating with a C-terminal HIS6 tag were expressed in *Escherichia coli*. After periplasmic extraction, dAb fusion proteins were purified via the C-terminal His6 tag. Fab expression was analysed by Western blotting of a non-reduced gel with anti- CH1 and anti-cKappa antibodies. FabA-dAb and FabA-didAb were expressed as full-length proteins and were shown to react to both antibody detection reagents.

Analysis of FabA-didAbs Expressed in *E. coli*

Further analysis was conducted to characterise the binding of HSA to FabA constructs to which one or more dAbs were fused. Binding assays were performed on a variety of constructs in which dAbL3 or dAbH4 fused to either the light or heavy chain of the FabA (see Table 8 for details of the constructs and summary of the binding data). Although constructs carrying only dAbH4, on either the light or heavy chain, were seen to bind HSA with comparatively poor affinity (≈9 μM and 3 μM respectively), higher affinity binding was observed for constructs carrying dAbL3, either as a single fusion (on either light or heavy chain) or partnered with a second dAb (dAbL3 or dAbH4) on the opposing chain.

TABLE 8

| Construct | $k_a$ (×10$^4$M$^{-1}$s$^{-1}$) | $k_d$ (×10$^{-3}$s$^{-1}$) | $K_D$ (×10$^{-9}$M) |
|---|---|---|---|
| FabA | — | — | nb |
| FabA-dAbL3 (LC-SG$_4$SE) | 4.46 | 16.2 | 363 |
| FabA-dAbH4 (LC SG$_4$SE) | — | — | 9142 |
| FabA-dAbL3 (HC-DKTHTS) | 8.24 | 15.4 | 187 |
| FabA-dAbH4 (HC-DKTHTS) | — | — | 2866 |
| FabA-didAb, -dAbL3 (LC-SG$_4$SE) & -dAbL3 (HC-DKTHTS) | 3.00 | 15.1 | 502 |
| FabA-didAb, -dAbL3 (LC-SG$_4$SE) & -dAbH4 (HC-DKTHTS) | 4.36 | 16.3 | 373 |

Affinity and kinetic parameters determined for the binding of HSA to FabAs carrying dAbL3 or dAbH4 on either light chain (LC) or heavy chain (HC) or both as indicated. No binding (nb) of HSA to the original FabA was detected. The interaction kinetics for the binding of HSA to the FabA with (dAbH4 on HC) or (dAbH4 on LC), were too rapid to determine, therefore affinity ($K_D$) was determined from steady-state binding.

What is claimed is:

1. A method for the treatment of a disease or disorder, comprising administering a therapeutically effective amount of a pharmaceutical composition comprising a dual specificity antibody fusion protein comprising an antibody Fab fragment or an antibody Fab' fragment with specificity for an antigen of interest, the fragment being fused to two single domain antibodies that have specificity for serum albumin,
  wherein one single domain antibody is fused to a C-terminus of a light chain of the Fab fragment or the Fab' fragment and the other single domain antibody is fused to a C-terminus of a heavy chain of the Fab fragment or the Fab' fragment, and
  wherein one single domain antibody is a VH domain comprising the sequence given in SEQ ID NO: 56 for CDRH 1, the sequence given in SEQ ID NO: 57 for CDR-H2 and the sequence given in SEQ ID NO: 58 for CDR-H3, and the other single domain antibody is a VL domain comprising the sequence given in SEQ ID NO: 59 for CDR-L1, the sequence given in SEQ ID NO: 60 for CDR-L2 and the sequence given in SEQ ID NO: 61 for CDR-L3, wherein the VH domain is fused to the C-terminus of the heavy chain of the Fab fragment or the Fab' fragment and the VL domain is fused to the C-terminus of the light chain of the Fab fragment or the Fab' fragment.

2. The method of claim 1, wherein the pharmaceutical composition additionally comprises other active ingredients and/or carriers.

3. The method of claim 1, wherein each single domain antibody humanised.

4. The method of claim 1, wherein the Fab or Fab' is fully human or humanised.

5. The method of claim 1, wherein each single domain antibody fused to the antibody Fab or Fab' fragment is fused via a linker of the amino acid sequence SEQ ID NO:1, SEQ ID NO:2, SEQ ID NO:3 or SEQ ID NO: 45.

6. The method of claim 1, in which the VH domain is linked to the C-terminus of the heavy chain of the Fab or Fab' fragment via a linker having the sequence given in SEQ ID NO: 2 or SEQ ID NO: 45 and the VL domain is linked to the C-terminus of the light chain of the Fab or Fab' fragment via a linker having the sequence given in SEQ ID NO: 1 or SEQ ID NO: 45.

7. The method of claim 1, wherein the serum albumin is human serum albumin.

8. The method of claim 1, wherein the disease or disorder is an inflammatory disease or disorder, an immune disease or disorder, a fibrotic disorder and/or a cancer;
- wherein the inflammatory disease or disorder and/or the immune disease or disorder comprise rheumatoid arthritis, psoriatic arthritis, still's disease, Muckle Wells disease, psoriasis, Crohn's disease, ulcerative colitis, SLE (Systemic Lupus Erythematosus), asthma, allergic rhinitis, atopic dermatitis, multiple sclerosis, vasculitis, Type I diabetes mellitus, transplantation and graft-versus-host disease;
- wherein the fibrotic disorder comprises idiopathic pulmonary fibrosis (IPF), systemic sclerosis (or scleroderma), kidney fibrosis, diabetic nephropathy, IgA nephropathy, hypertension, end-stage renal disease, peritoneal fibrosis (continuous ambulatory peritoneal dialysis), liver cirrhosis, age-related macular degeneration (ARMD), retinopathy, cardiac reactive fibrosis, scarring, keloids, burns, skin ulcers, angioplasty, coronary bypass surgery, arthroplasty and cataract surgery; and
- wherein the cancer comprises (i) a malignant new growth that arises from epithelium, found in skin or the lining of breast, ovary, prostate, lung, kidney, pancreas, stomach, bladder or bowel and/or (ii) bone, liver, lung or brain cancer.

* * * * *